US012215349B2

(12) United States Patent
Vizcardo et al.

(10) Patent No.: US 12,215,349 B2
(45) Date of Patent: Feb. 4, 2025

(54) METHODS OF PREPARING AN ISOLATED OR PURIFIED POPULATION OF THYMIC EMIGRANT CELLS AND METHODS OF TREATMENT USING SAME

(71) Applicant: The United States of America, as represented by the Secretary, Department of Health and Human Services, Bethesda, MD (US)

(72) Inventors: Raul E. Vizcardo, Derwood, MD (US); Nicholas D. Klemen, Carmel, IN (US); Nicholas P. Restifo, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 646 days.

(21) Appl. No.: 16/468,890

(22) PCT Filed: Dec. 13, 2017

(86) PCT No.: PCT/US2017/065986
§ 371 (c)(1),
(2) Date: Jun. 12, 2019

(87) PCT Pub. No.: WO2018/111981
PCT Pub. Date: Jun. 21, 2018

(65) Prior Publication Data
US 2020/0080057 A1    Mar. 12, 2020

Related U.S. Application Data

(60) Provisional application No. 62/433,591, filed on Dec. 13, 2016.

(51) Int. Cl.
*C12N 5/0783*    (2010.01)
*A61K 39/00*     (2006.01)
*A61P 35/00*     (2006.01)

(52) U.S. Cl.
CPC .......... *C12N 5/0637* (2013.01); *A61K 39/461* (2023.05); *A61K 39/4611* (2023.05); *A61K 39/4632* (2023.05); *A61K 39/464499* (2023.05); *A61P 35/00* (2018.01); *C12N 5/0636* (2013.01); *C12N 5/0638* (2013.01); *C12N 2502/1185* (2013.01); *C12N 2506/45* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 7,575,925 B2 | 8/2009 | Schmitt et al. | |
| 7,820,174 B2 | 10/2010 | Wang et al. | |
| 8,034,334 B2 | 10/2011 | Dudley et al. | |
| 8,216,565 B2 | 7/2012 | Restifo et al. | |
| 8,383,099 B2 | 2/2013 | Dudley et al. | |
| 8,465,743 B2 | 6/2013 | Rosenberg et al. | |
| 8,741,648 B2 * | 6/2014 | Rajesh | C12N 15/86 435/377 |
| 8,785,601 B2 | 7/2014 | Rosenberg et al. | |
| 2004/0171148 A1 * | 9/2004 | Schmitt | C12N 5/0636 435/372 |
| 2008/0064101 A1 * | 3/2008 | Pykett | C12N 5/0636 435/373 |
| 2012/0101148 A1 | 4/2012 | Aking et al. | |
| 2012/0244133 A1 | 9/2012 | Rosenberg et al. | |
| 2012/0301438 A1 * | 11/2012 | Cheng | C12N 5/0696 435/465 |
| 2013/0078226 A1 * | 3/2013 | Nakauchi | C12N 5/0638 435/372.3 |
| 2013/0274203 A1 | 10/2013 | Morgan et al. | |
| 2014/0037628 A1 | 2/2014 | Morgan et al. | |
| 2014/0248248 A1 * | 9/2014 | Zuniga-Pflucker | A61P 31/18 435/29 |
| 2014/0274909 A1 | 9/2014 | Orentas et al. | |
| 2016/0369237 A1 * | 12/2016 | West | C12N 5/0652 |
| 2019/0142867 A1 * | 5/2019 | Zandstra | C12N 5/0647 435/377 |
| 2020/0405767 A1 * | 12/2020 | Gay | A61K 31/4409 |
| 2021/0161964 A1 * | 6/2021 | Feng | C12N 5/0644 |
| 2021/0289769 A1 * | 9/2021 | Zeitlin | A61P 43/00 |
| 2023/0248769 A1 * | 8/2023 | Bae | C07K 14/70578 424/85.5 |

FOREIGN PATENT DOCUMENTS

WO    2017/075389 A1    5/2017
WO    2018/111981 A1    6/2018

OTHER PUBLICATIONS

Nishimura et al Cell Stem Cell, 2013, v.12 p. 114-126).*
Nishimura et al Cell stem cell, 2013, v. 12 pp. 114-126.*
Aasen et al., "Efficient and rapid generation of induced pluripotent stem cells from human keratinocytes," *Nat. Biotechnol.*, 26(11): 1276-1284 (2008).
Anderson et al., "Fetal thymus organ culture," *Cold Spring Harbor Protocols*, (8): pdb-prot4808, 6 pp. (2007).
Awong et al., "Characterization in vitro and engraftment potential in vivo of human progenitor T cells generated from hematopoietic stem cells," *Blood*, 114(5): 972-982 (2009).

(Continued)

*Primary Examiner* — Michail A Belyavskyi
(74) *Attorney, Agent, or Firm* — Leydig, Voit & Mayer, Ltd.

(57) ABSTRACT

Disclosed are methods of preparing thymic emigrant cells in vitro, isolated or purified thymic emigrant cells prepared by the methods, and pharmaceutical compositions comprising the same. Further disclosed are methods of treating or preventing a condition in a mammal comprising administering the thymic emigrant cells or pharmaceutical compositions comprising the same to the mammal.

10 Claims, 10 Drawing Sheets

Specification includes a Sequence Listing.

(56) References Cited

OTHER PUBLICATIONS

3D Biomatrix™, "3D Cell Culture: An Early-Stage Oncology Drug Discovery Tool—3D cell culture to enhance physiological relevance of cell-based assays," White Paper, 13 pp. (2012).
Best et al., "Transcriptional insights into the CD8+ T cell response to infection and memory T cell formation," Nat. Immunol., 14(4): 404-412 (2013).
Borgulya et al., "Exclusion and inclusion of α and β T Cell receptor alleles," Cell, 69: 529-537 (1992).
Brauer et al., "T Cell Genesis: In Vitro Veritas Est?," Trends in Immunology, 37(12): 889-901 (2016).
Carpenter et al., "Decision checkpoints in the thymus," Nat. Immunol,, 11(8): 666-673 (2010).
Cheng et al., "Multiplexed activation of endogenous genes by CRISPR-on, an RNA-guided transcriptional activator system," Cell Res, 23: 1163-1171 (2013).
Codaleda et al., "Conversion of mature B cells into T cells by dedifferentiation to uncommitted progenitors," Nature, 449: 473-479 (2007).
Crompton et al., "Memoirs of a Reincarnated T Cell," Cell Stem Cell, 12(1): 6-8 (2013).
Crompton et al., "Reprogramming antitumor immunity," Trends in Immunology, 35(4): 178-185 (2014).
European Patent Office, International Search Report in International Patent Application No. PCT/US2017/065986, mailed Mar. 9, 2018.
European Patent Office, Written Opinion in International Patent Application No. PCT/US2017/065986, mailed Mar. 9, 2018.
Fink, "The biology of recent thymic emigrants," Annu. Rev. Immunol., 31: 31-50 (2013).
Fusaki et al., "Efficient induction of transgene-free human pluripotent stem cells using a vector based on Sendai virus, an RNA virus that does not integrate into the host genome," Proceedings of the Japan Academy, Series B, 85(5): 348-362 (2009).
Galic et al., "T lineage differentiation from human embryonic stem cells," PNAS, 103(31): 11742-11747 (2006).
Gattinoni, et al., "Paths to stemness: building the ultimate antitumour T cell," Nat. Rev. Cancer, 12(10): 671-684 (2012).
Gommans, "Engineering zinc finger protein transcription factors: The therapeutic relevance of switching endogenous gene expression on or off at command," J. Mol. Biol., 354(3): 507-519 (2005).
Haase et al., "Generation of Induced Pluripotent Stem Cells from Human Cord Blood," Cell Stem Cell, 5(4): 434-441 (2009).
Hanna et al., "Somatic cell reprogramming and transitions between pluripotent states: facts, hypotheses, unresolved issues," Cell, 143(4): 508-525 (2010).
Hogquist et al., "T Cell Adolescence: Maturation events beyond positive selection," The Journal of Immunology, 195(4): 1351-1357 (2015).
Hou et al., "Pluripotent Stem Cells Induced from Mouse Somatic cells by Small-Molecule Compounds," Science, 341(6146): 651-654 (2013).
Irizarry et al., "Exploration, normalization, and summaries of high density oligonucleotide array probe level data," Biostatistics, 4(2): 249-264 (2003).
Jopling, "Dedifferentiation, transdifferentiation and reprogramming: three routes to regeneration," Nat. Rev. Mol. Cell Biol., 12: 79-89 (2011).
Kidder, "Generation of induced pluripotent stem cells using chemical inhibition and three transcription factors," Stem Cell Transcriptional Networks: Methods and Protocols, Methods in Molecular Biology, 1150: 227-236 (2014).
Kidder et al., "Extended Self-Renewal and Accelerated Reprogramming in the Absence of Kdm5b," Molecular and Cellular Biology, 33(24): 4793-4810 (2013).
Kim, "Direct reprogramming of human neural stem cells by OCT4," Nature, 461: 649-654 (2009).
Kitamura et al., "Retrovirus-mediated gene transfer and expression cloning: Powerful tools in functional genomics," Experimental Hematology, 31(11): 1007-1014 (2003).
Klebanoff et al., "Central memory self/tumor-reactive CD8+ T Cells confer superior antitumor immunity compared with effector memory T cells," PNAS, 102(27): 9571-9576 (2005).
Lei et al., "T lineage differentiation from induced pluripotent stem cells," Cell. Immunol., 260: 1-5 (2009).
Lowry et al., "Generation of human induced pluripotent stem cells from dermal fibroblasts," PNAS, 105(8): 2883-2888 (2008).
Morita et al., "Plat-E: an efficient and stable system for transient packaging of retroviruses," Gene Therapy, 7(12): 1063-1066 (2000).
Nishimura et al., "Generation of rejuvenated antigen-specific T cells by reprogramming to pluripotency and redifferentiation," Cell Stem Cell, 12(1): 114-126 (2013).
Ogle et al., "Biological implications of cell fusion," Nat. Rev. Mol. Cell Biol., 6: 567-575 (2005).
Overwijk et al., "gp100/pmel 17 is a Murine tumor rejection antigen: Induction of 'Self'-reactive, tumoricidal T cells using high-affinity, altered peptide ligand," The Journal of Experimental Medicine, 188(2): 277-286 (1998).
Overwijk et al., "Tumor regression and autoimmunity after reversal of a functionally tolerant state of self-reactive CD8+ T cells," The Journal of Experimental Medicine, 198(4): 569-580 (2003).
Rivière et al., "Variable correction of Artemis deficiency by I-Sce 1-meganuclease-assisted homologous recombination in murine hematopoietic stem cells," Gene Therapy, 21(5): 529-532 (2014).
Schmitt et al., "Induction of T cell development and establishment of T cell competence from embryonic stem cells differentiated in vitro," Nat. Immunol., 5(4): 410-417 (2004).
Schmitz et al., "Gene expression analysis of thymocyte selection in vivo," International Immunology, 15(10): 1237-1248 (2003).
Serwold et al., "Early TCR expression and aberrant T cell development in mice with endogenous prerearranged T cell receptor genes," The Journal of Immunology, 179(2): 928-938 (2007).
Smith et al., "Concise Review: In Vitro T-cell generation from adult, embryonic, and induced pluripotent stem cells: Many Roads to One Destination," Stem Cells, 33(11): 3174-3180 (2015).
Stadtfeld et al., "Induced pluripotency: history, mechanisms, and applications," Genes & Development, 24(20): 2239-2263 (2010).
Szabo et al., "Direct conversion of human fibroblasts to multilineage blood progenitors," Nature, 468: 521-529 (2010).
Takahama et al., "Positive selection of CD4+ T cells by TCR ligation without aggregation even in the absence of MHC," Nature, 371: 67-70 (1994).
Takahashi et al., "Induction of pluripotent stem cells from mouse embryonic and adult fibroblast cultures by defined factors," Cell, 126(4): 663-676 (2006).
Takahashi et al., "Induction of pluripotent stem cells from adult human fibroblasts by defined factors," Cell, 131: 861-872 (2007).
Tarca et al., "A novel signaling pathway impact analysis," Bioinformatics, 25(1): 75-82 (2009).
Themeli et al., "New cell sources for T cell engineering and adoptive immunotherapy," Cell Stem Cell, 16(4): 357-366 (2015).
Themeli et al., "Generation of tumor-targeted human T lymphocytes from induced pluripotent stem cells for cancer therapy," Nature Biotechnology, 31(10): 928-935 (2013).
Tsai et al., "Single transcription factor reprogramming of hair follicle dermal papilla Cells to induced pluripotent stem cells," Stem Cells, 29(6): 964-971 (2011).
Ueno et al., "Development of T-Lymphocytes in mouse fetal thymus organ culture," Basic Cell Culture Protocols, Humana Press, 117-133 (2005).
Veldman et al., "Hidden chromosome abnormalities in haematological malignancies detected by multicolour spectral karyotyping," Nat. Genet., 15: 406-410 (1997).
Vizcardo et al., "Generation of Tumor Antigen-Specific iPSC-Derived Thymic Emigrants Using a 3D Thymic Culture System," Cell Reports, 22: 3175-3190 (2018).
Vizcardo et al., "Regeneration of Human Tumor Antigen-Specific T Cells from iPSCs Derived from Mature CD8+ T Cells," Cell Stem Cell, 12(1): 31-36 (2013).
Vizcardo et al., "A Three-Dimensional Thymic Culture System to Generate Murine Induced Pluripotent Stem Cell-derived Tumor Antigen-specific Thymic Emigrants," Journal of Visualized Experiments, 150:e58672 (2019).

(56) References Cited

OTHER PUBLICATIONS

Von Boehmer, "Unique features of the pre-T-cell receptor α-chain: not just a surrogate," *Nat. Rev. Immunol.*, 5: 571-577 (2005).

Wilmut et al., "Viable offspring derived from fetal and adult mammalian cells," *Nature*, 385: 810-813 (1997).

Xie et al., "Stepwise Reprogramming of B cells into Macrophages," *Cell*, 117(5): 663-676 (2004).

Xing et al., "Late stages of T cell maturation in the thymus involve NF-κB and tonic type I interferon signaling," *Nat. Immunol.*, 17(5): 565-573 (2016).

Xiong et al., "Development and selection of γδ T cells," *Immunol. Rev.*, 215: 15-31 (2007).

Yamagata et al., "Self-reactivity in thymic double-positive cells commits cells to a CD8αα lineage with characteristics of innate immune cells," *Nat. Immunol.*, 5(6): 597-605 (2004).

Yu et al., "Induced pluripotent stem cell lines derived from human somatic cells," Science, 318(5858): 1917-1920 (2007).

Yuan et al., "Lin28b reprograms adult bone marrow hematopoietic progenitors to mediate fetal-like lymphopoiesis," Science, 335(6073): 1195-1200 (2012).

Zhang, "Programmable sequence-specific transcriptional regulation of mammalian genome using designer TAL effectors," *Nature Biotechnol.*, 29(2): 149-153 (2011), Author Manuscript.

Zhao et al., "Extrathymic generation of tumor-specific T cells from genetically engineered human hematopoietic stem cells via notch signaling," *Cancer Res.*, 67(6): 2425-2429 (2007).

Zhou et al., "Extreme makeover: Converting one cell into another," *Cell Stem Cell*, 3(4): 382-388 (2008).

Parent et al., "Generation of Functional Thymic Epithelium from Human Embryonic Stem Cells that Supports Host T Cell Development", *Cell Stem Cell* 13: 219-229 (2013).

Sun et al., "Directed Differentiation of Human Embryonic Stem Cells into Thymic Epithelial Progenitor-like Cells Reconstitutes the Thymic Microenvironment In Vivo", *Cell Stem Cell* 13: 230-236 (2013).

\* cited by examiner

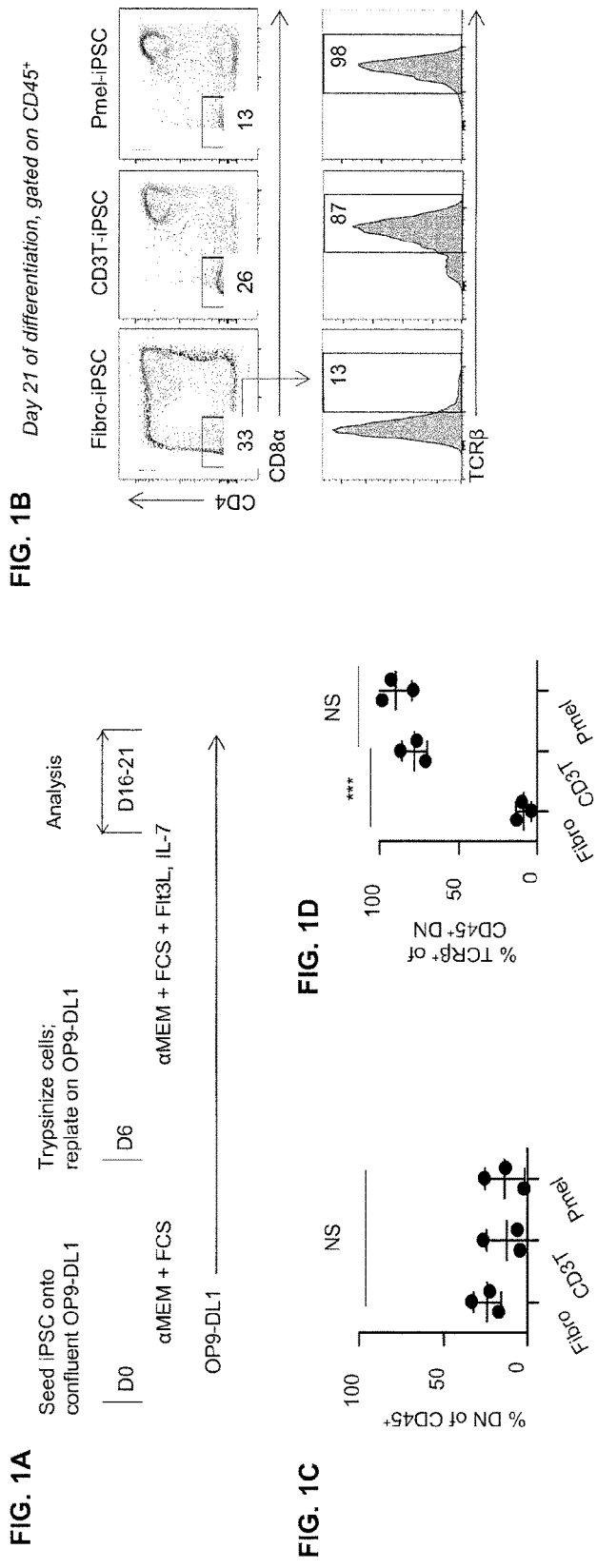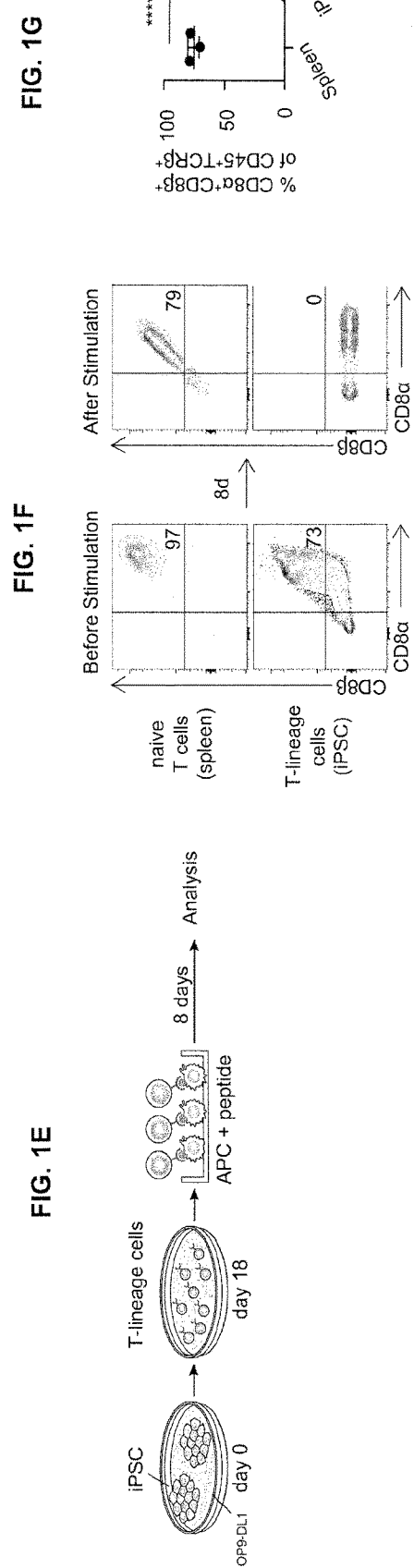

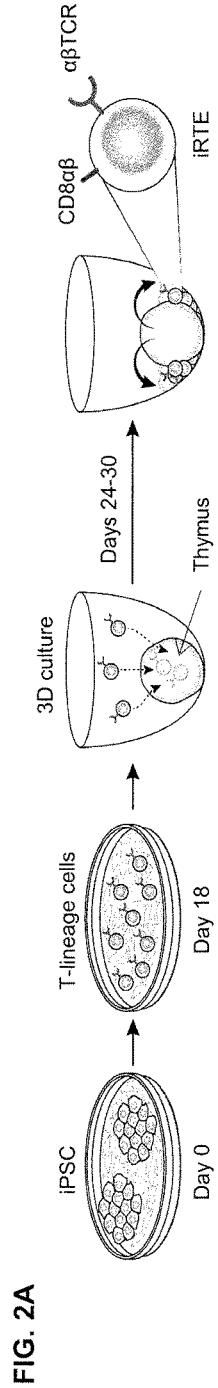
FIG. 2A
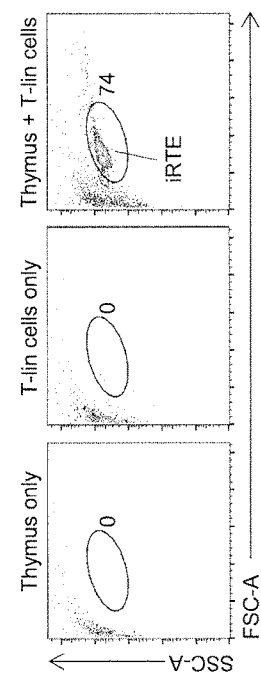
FIG. 2B
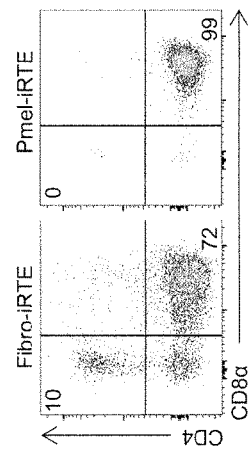
FIG. 2C
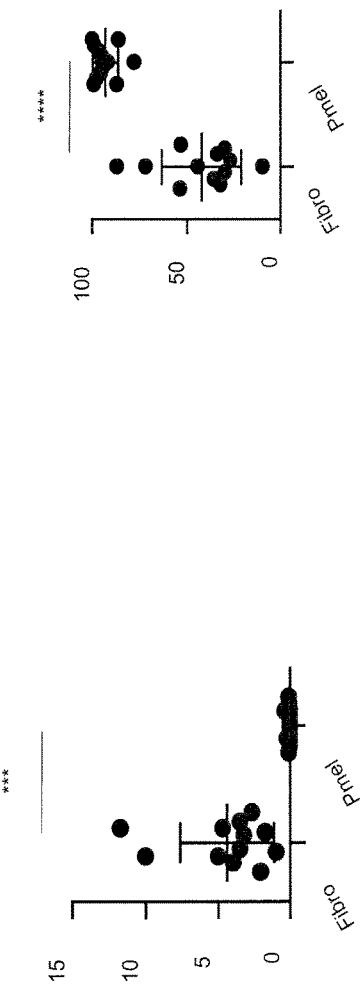
FIG. 2D
FIG. 2E

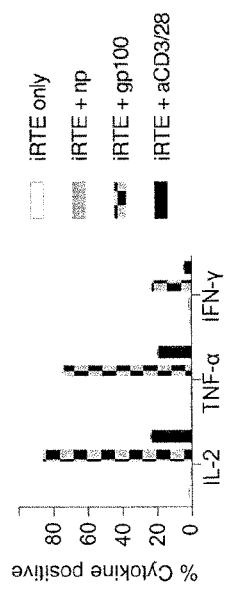
FIG. 3A
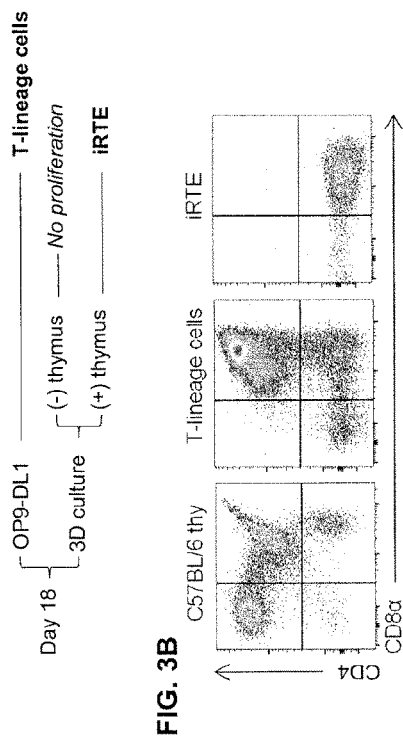
FIG. 3B
FIG. 3C
FIG. 3E
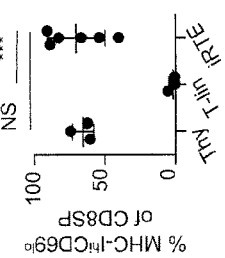
FIG. 3D
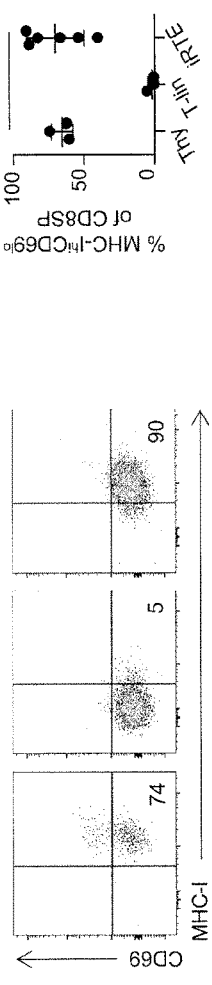
FIG. 3F
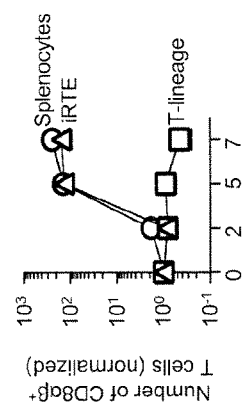
FIG. 3G
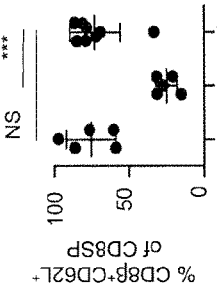
FIG. 3H
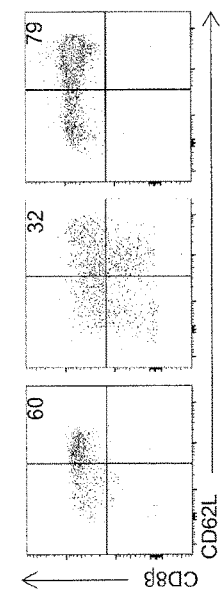
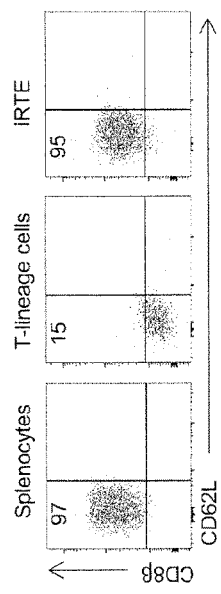
FIG. 3I

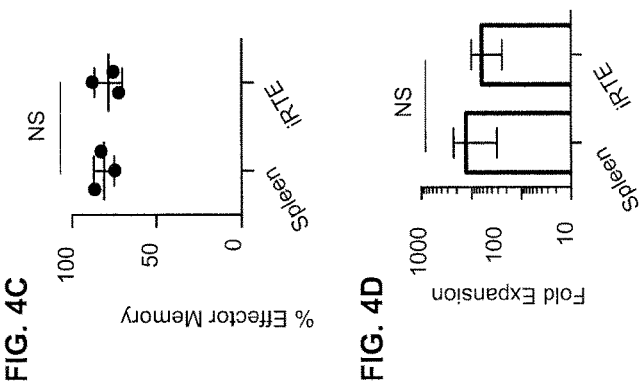
FIG. 4A
FIG. 4B
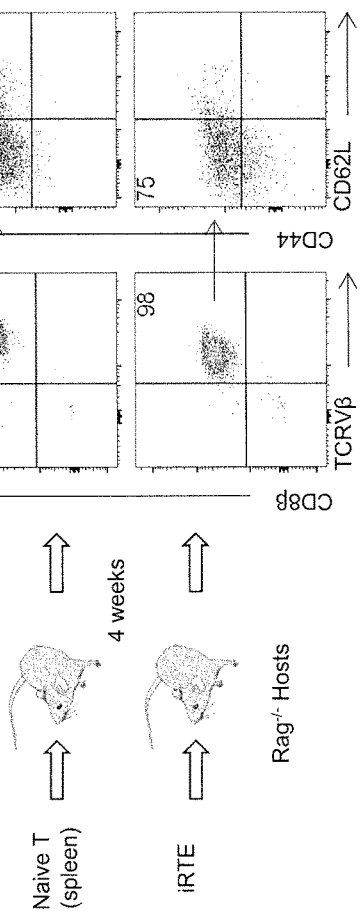
FIG. 4C
FIG. 4D
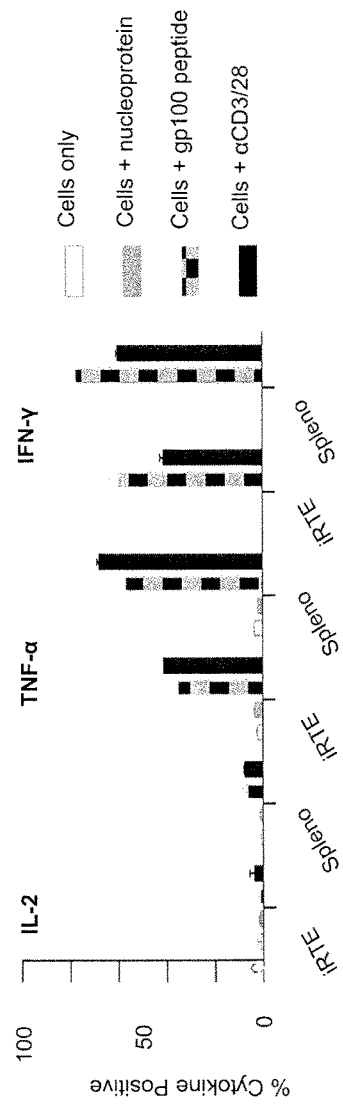
FIG. 4E

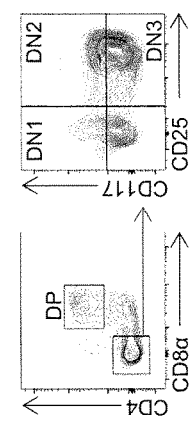
FIG. 6A
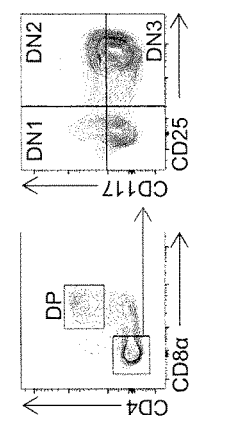
FIG. 6B
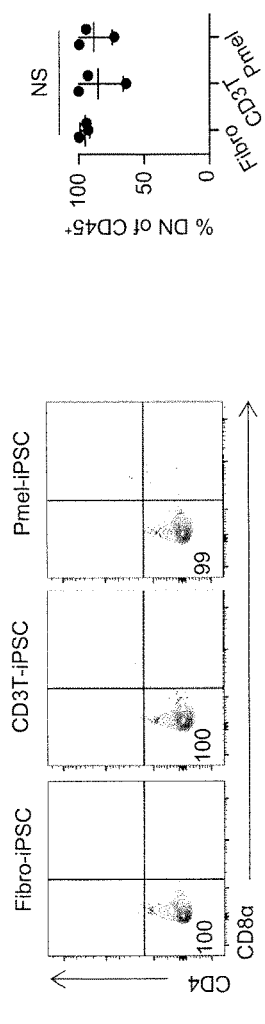
FIG. 6C
FIG. 6D
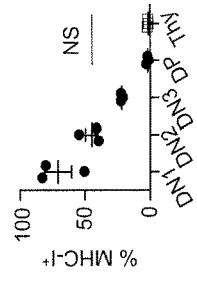
FIG. 6E
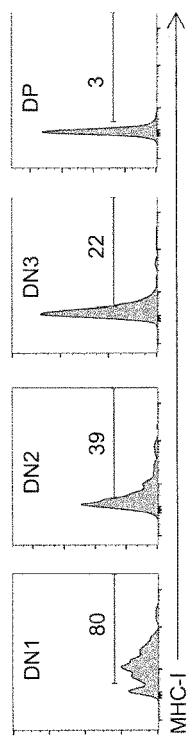
FIG. 6F

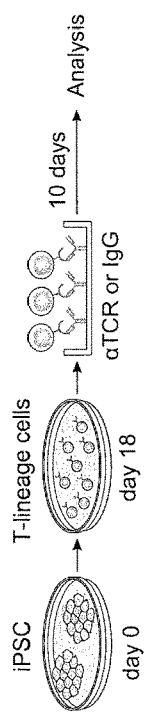
FIG. 7A
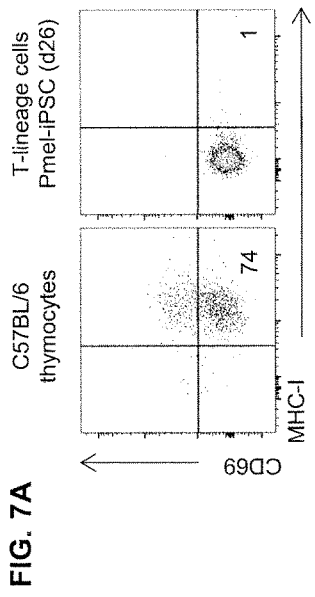
FIG. 7B
FIG. 7C
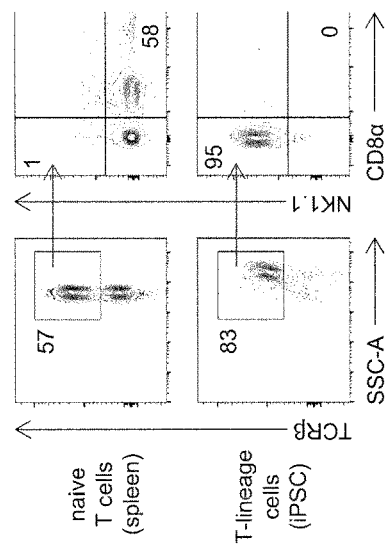
FIG. 7D
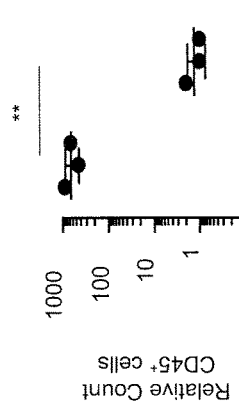
FIG. 7E
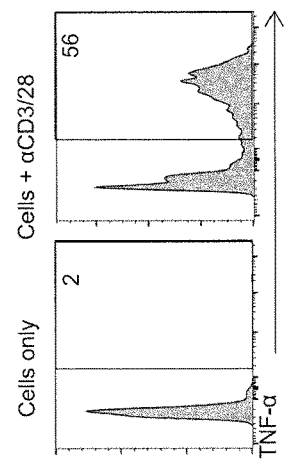

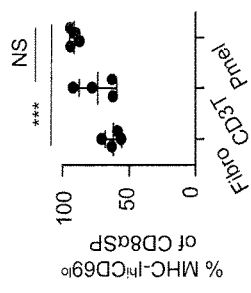
FIG. 8A
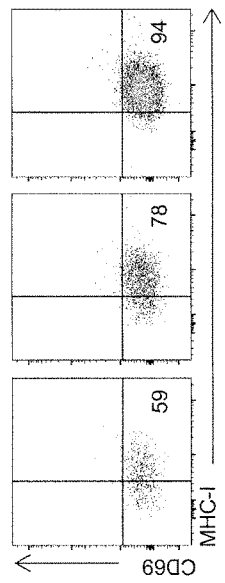
FIG. 8B
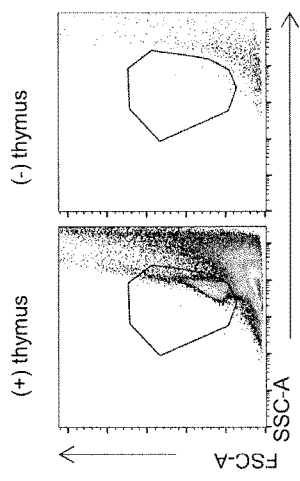
FIG. 8C
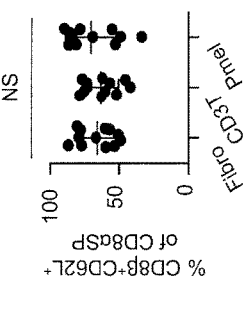
FIG. 8E
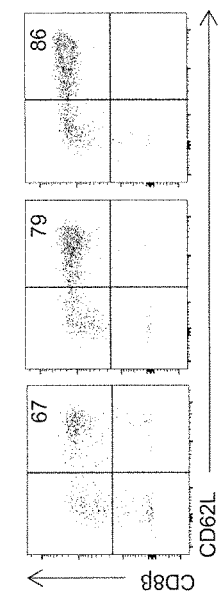
FIG. 8G
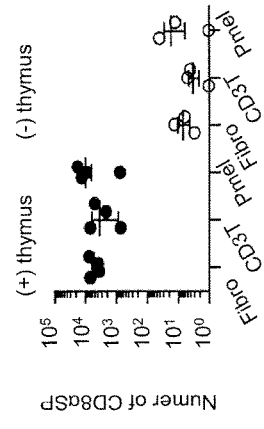
FIG. 8D
FIG. 8F
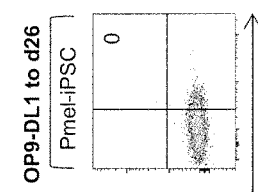
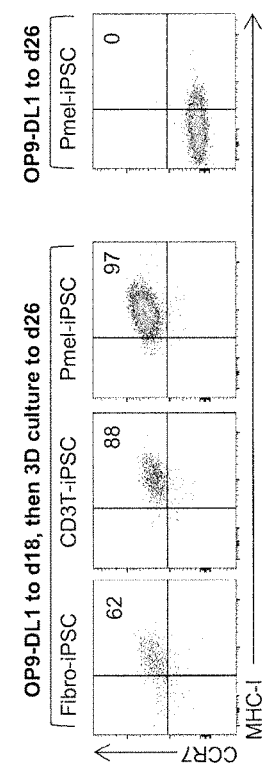
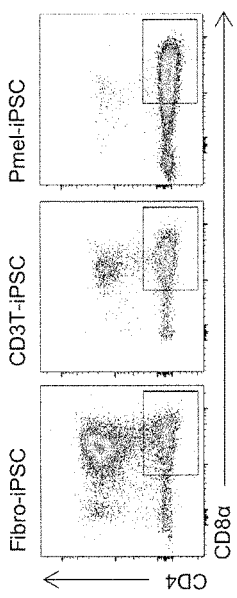
FIG. 8H

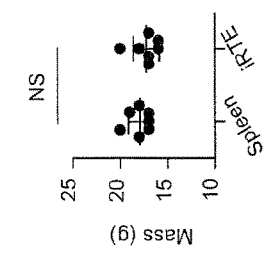
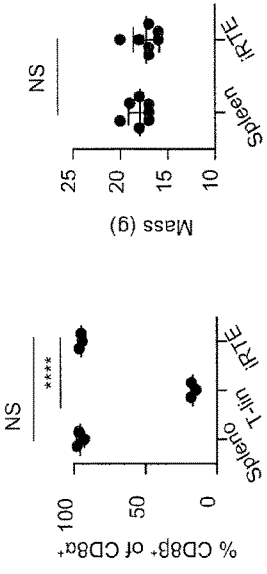
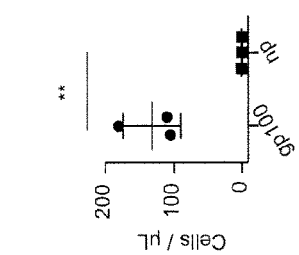
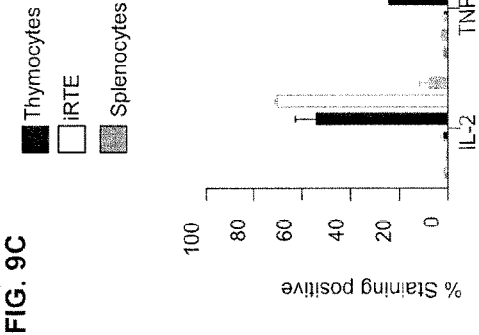
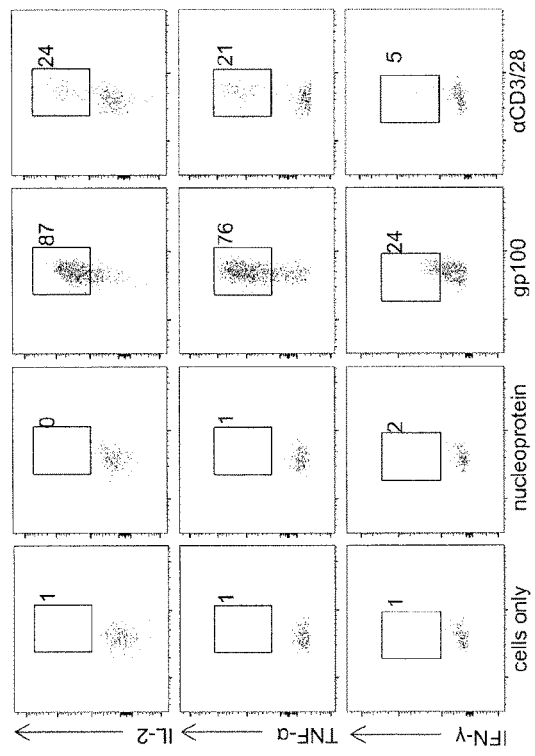
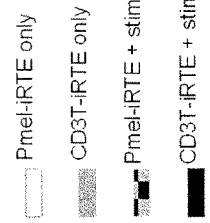
FIG. 9A
FIG. 9B
FIG. 9C
FIG. 9D
FIG. 9E
FIG. 9F

METHODS OF PREPARING AN ISOLATED OR PURIFIED POPULATION OF THYMIC EMIGRANT CELLS AND METHODS OF TREATMENT USING SAME

CROSS-REFERENCE TO RELATED APPLICATIONS

This patent application is a U.S. National Phase Patent Application of International Patent Application No. PCT/US2017/065986, filed Dec. 13, 2017, which claims the benefit of U.S. Provisional Patent Application No. 62/433,591, filed Dec. 13, 2016, both of which are hereby incorporated by reference in their entireties.

STATEMENT REGARDING FEDERALLY SPONSORED RESEARCH AND DEVELOPMENT

This invention was made with Government support under project number ZIABC010763-12 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One xxx Byte ASCII (Text) file named "743296 ST25.txt." dated Jun. 13, 2019.

BACKGROUND OF THE INVENTION

Adoptive cell therapy (ACT) can produce positive clinical responses in some cancer patients. Nevertheless, obstacles to the successful use of ACT for the widespread treatment of cancer and other conditions remain. For example, the efficacy of ACT may be compromised if T cells are terminally differentiated. Accordingly, there is a need for improved methods of cells for ACT.

BRIEF SUMMARY OF THE INVENTION

An embodiment of the invention provides a method of preparing an isolated or purified population of thymic emigrant cells in vitro, comprising: modifying source cells into pluripotent cells, multipotent cells, or T-lineage cells; culturing the pluripotent cells, multipotent cells, or T-lineage cells in the presence of a Notch receptor agonist to produce $CD45^+$ cells; culturing the $CD45^+$ cells in the presence of thymic tissue, wherein culturing the $CD45^+$ cells in the presence of thymic tissue comprises migrating the cells into the thymic tissue; egressing the cells from the thymic tissue, wherein the cells egressing from the thymic tissue are thymic emigrant cells; and isolating the thymic emigrant cells from the thymic tissue, wherein the thymic emigrant cells are $CD8\alpha^+CD8\beta^+CD4^-$ or $CD8\alpha^-CD8\beta^-CD4^+$.

Further embodiments of the invention provide an isolated or purified population of thymic emigrant cells prepared by the inventive method and pharmaceutical compositions comprising the same.

Another embodiment of the invention provides a method of treating or preventing a condition in a mammal, the method comprising administering to the mammal the inventive population of cells or the inventive pharmaceutical composition in an amount effective to treat or prevent the condition in the mammal.

BRIEF DESCRIPTION OF THE SEVERAL VIEWS OF THE DRAWING(S)

FIG. 1A is a schematic illustrating the OP9-DL1 co-culture system to induce iPSC differentiation into T-lineage cells ("D"="Day").

FIG. 1B illustrates the results of a flow cytomtery analysis measuring the expression of CD4 and $CD8\alpha$ by iPSC differentiated for 21 days, gated on $CD45^+$. Histograms are gated on $CD45^+CD4^-CD8\alpha^-$ (double negative, DN) cells.

Figure 5A:
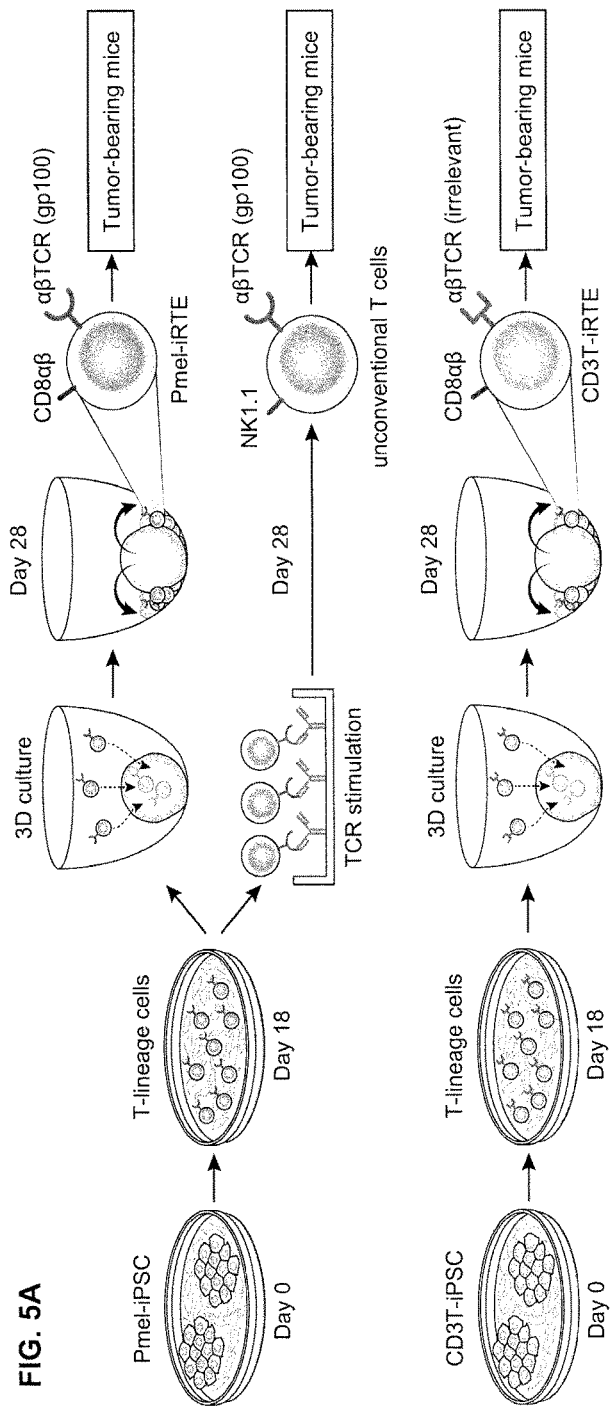

FIG. 1C is a graph showing the percentage of $CD45^+$ cells that are DN on day 21. Values represent mean±SEM (n=3, using an unpaired t test *$p<0.001$, **$p<0.0001$; NS indicates no significant difference).

FIG. 1D is a graph showing the percentage of $CD45^+$ DN cells expressing $TCR\alpha$ on day 21 (n=3).

FIG. 1E is a schematic illustrating the differentiation of Pmel-iPSC for 18 days in OP9-DL1, followed by stimulation and analysis.

FIG. 1F shows flow cytomtery dot plots showing the phenotype before and after stimulation, gated on $CD45^+$ $TCR\beta^+$.

FIG. 1G is a graph showing the percentage of $CD8\alpha^+$ T cells expressing $CD8\beta$ after expansion, gated as in FIG. 1F (n=3).

FIG. 2A is a schematic illustrating iPSC differentiation and 3D thymic culture.

FIG. 2B shows flow cytometry dots plot illustrating the SSC-A and FSC-A expression detected in recovered 3D culture media in thymus only, T-lineage cells only, or T-lineage cells cultured in thymus.

FIG. 2C shows flow cytometry dot plots illustrating the expression of CD4 and $CD8\alpha$ detected in fibro-iRTE or Pmel-iRTE. Plots are gated on $CD45^+$ and $TCR\beta^+$.

FIG. 2D is a graph showing the percentage of $TCR\beta^+$ $CD4^+CD8\alpha^-$ (CD4SP) iRTE produced from Fibro-iPSC and Pmel-iPSC. Values represent mean±SEM (n=12, *$p<0.001$, **$p<0.0001$).

FIG. 2E is a graph showing the percentage of $TCR\beta^+$ $CD4^-CD8\alpha^+$ ($CD8\alpha SP$) iRTE produced from Fibro-iPSC and Pmel-iPSC. Values represent mean±SEM (n=12, *$p<0.001$, **$p<0.0001$).

FIG. 3A is a schematic illustrating cell generation from iPSC.

FIG. 3B shows flow cytometry dot plots illustrating the expression of CD4 and $CD8\alpha$ in C57BL/6 adult thymocytes, T-lineage cells produced on OP9-DL1 and Pmel-iRTE. Plots are gated on $CD45^+$ and a dump gate excludes NK1.1, $TCR\gamma\delta$, CD44 and CD25.

FIG. 3C shows flow cytometry dot plots illustrating the expression of CD69 and MHC-I of the cells in FIG. 3B. The analysis is of $TCR\beta^+CD8\alpha SP$-gated cells.

FIG. 3D is a graph showing the percentage of $CD69^-$ and $MHC-I^+$ cells gated for $TCR\beta^+CD8\alpha SP$ cells. Values represent mean±SEM (n=3 for thymocytes, n=6 for iRTE, NS indicates no significant difference).

FIG. 3E shows flow cytometry dot plots illustrating the expression of CD62L and $CD8\beta$ of the cells in FIG. 3B. The analysis is of $TCR\beta^+CD8\alpha SP$-gated cells.

FIG. 3F is a graph showing the percentage of $CD62L^+$ $CD8\beta^+$ cells gated for $TCR\beta^+CD8\alpha SP$ cells. Values represent mean±SEM (n=5 for thymocytes, n=8 for iRTE, NS indicates no significant difference).

FIG. 3G is a graph illustrating the measurement of cytokine production following stimulation of Pmel-iRTE for 6 hours (n=3). Values represent mean±SEM (n=3).

FIG. 3H is a graph showing the expansion of CD8αβ⁺ T cells in response to peptide stimulation, with relative values shown on a $\log_{10}$ scale. The count does not include CD8α⁺ or DN T cells.

FIG. 3I shows flow cytometry dot plots measuring the expression of CD8β and CD62L of cells on day 7, gated on TCRβ⁺CD8αSP.

FIG. 4A is a schematic illustrating the transfer of equal numbers of naïve splenocytes and Pmel-iRTE into $Rag^{-/-}$ hosts.

FIG. 4B shows flow cytometry dot plots detecting the expression of CD8β, TCRVβ, CD44, and CD62L in peripheral blood after 4 weeks. Plots are gated on CD45⁺CD8α⁺.

FIG. 4C is a graph showing the percentage of spleen or iRTE cells with an effector memory (CD44⁺CD62L⁻) phenotype. Values represent mean±SD (n=3, NS indicates no significant difference).

FIG. 4D is a graph showing the fold expansion in vivo after transfer of spleen or iRTE cells. To increase statistical power, two pooled experiments are shown. Values represent mean±SD (n=6, NS indicates no significant difference).

FIG. 4E shows graphs showing the percentages of cells positive for expression of IL-2, TNF-α, or IFN-γ following stimulation of cells ex vivo. Values represent mean±SEM (n=3).

FIG. 5A is a schematic illustrating the experiment testing the ability of Pmel-iRTE, unconventional T cells, and CD3T-iRTE to treat tumor-bearing mice.

Figure 5C:
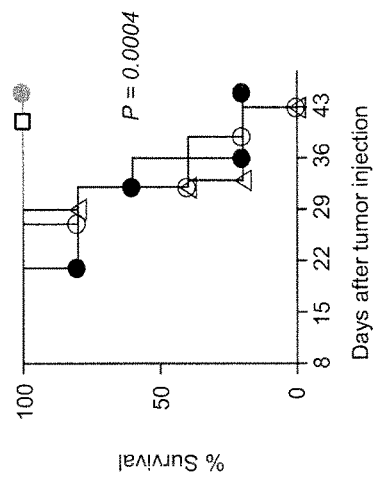
Figure 5B:
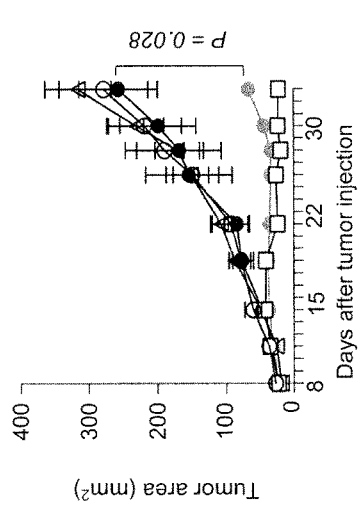

FIG. 5B is a graph showing the cross sectional area (mm²) of subcutaneous tumors measured in mice treated as indicated at various time points (days) after tumor injection. Cohorts of mice received Pmel-iRTE (grey circles), CD3T-iRTE (black circles), unconventional T cells generated from Pmel-iPSC (triangles), naïve splenocytes (squares), or vehicle (unshaded circles). Values represent mean±SEM (n=5). A Wilcoxon Rank Sum Test was used to compare tumor area of cohorts receiving Pmel-iRTE and CD3T-iRTE.

FIG. 5C is a graph showing the percentage of tumor-bearing mice surviving following treatment as indicated in FIG. 5B at various time points (days) after tumor injection. Cohorts of mice received Pmel-iRTE (grey circles), CD3T-iRTE (black circles), unconventional T cells generated from Pmel-iPSC (triangles), naïve splenocytes (squares), or vehicle (unshaded circles). The survival data are represented as Kaplan-Meier curves. A Mantel-Cox test was used to compare the survival of cohorts receiving Pmel-iRTE and CD3T-iRTE.

FIG. 6A shows flow cytometry plots illustrating the phenotype of iPSC differentiated in vitro for 16 days. Plots are gated on CD45⁺.

FIG. 6B is a graph illustrating the percentage of CD45⁺ cells that were DN on day 16. Values represent mean±SEM (n=3, NS indicates no significant difference).

FIG. 6C shows flow cytometry dot plots illustrating the phenotype of iPSC differentiated in vitro for 18 days. Plots are gated on CD45⁺ TCRβ⁺. Thymocytes from a C57BL/6 adult mouse are shown for comparison. Plots with CD8β and CD62L are gated on DP (CD4⁺CD8α⁺) or CD8αSP (CD4⁻CD8α⁺) T cells.

FIG. 6D shows flow cytometry plots illustrating the phenotype of iPSC differentiated in vitro for 18 days. Gating on DN T cells, CD117 and CD25 identifies DN1-DN3 subsets.

FIG. 6E is a graph showing MHC-I expression by the indicated subsets, with C57BL/6 DP thymocytes shown for comparison. Values represent mean±SD (n=3, NS indicates no significant difference).

FIG. 6F shows histograms showing MHC-I expression by the indicated cell subsets.

FIG. 7A shows flow cytometry dot plots illustrating the phenotype of iPSC differentiated for 26 days on OP9-DL1, with C57BL/6 thymocytes for comparison. Plots are gated on TCRβ⁺CD8αSP.

FIG. 7B is a graph showing the relative number of CD45⁺ TCRβ⁺ T cells on a log 10 scale (note: most cells were CD8α⁺ or DN, as shown in FIG. 1F). Pmel-iPSC were differentiated for 18 days and then stimulated with cognate or irrelevant peptide.

FIG. 7C are histograms showing cytokine production following stimulation of CD8α⁺ T cells using αCD3/28.

FIG. 7D is a schematic illustrating the differentiation of iPSC for 18 days followed by stimulation with plate-bound αTCR antibody.

FIG. 7E shows flow cytometry plots illustrating the phenotype of T-lineage cells and naïve splenocytes after stimulation as in FIG. 7D. The plots are gated on CD45⁺.

FIG. 8A shows flow cytometry dot plots illustrating the phenotype of iPSC differentiated for 18 days and transferred to 3D cultures with or without thymic lobes. A representative plot from each condition is shown.

FIG. 8B is a graph showing the absolute number of TCRβ⁺CD8αSP cells in 3D cultures with or without thymic lobes, shown using a log 10 scale. Values represent mean±SD (n=4 for 3D cultures with a thymus, n=3 for 3D cultures without a thymus).

FIG. 8C shows flow cytometry dot plots illustrating the phenotype of cells in 3D thymic cultures. Plots are gated on CD45⁺ and a dump gate excludes NK1.1, TCRγδ, CD44 and CD25.

FIG. 8D shows flow cytometry dot plots illustrating the phenotype of TCRβ⁺CD8αSP gated cells in 3D cultures.

FIG. 8E is a graph showing the percentage of CD69⁻ and MHC-I⁺ cells as in FIG. 8D. Values represent mean±SEM (n=4, ***p<0.001, NS indicates no significant difference).

FIG. 8F shows flow cytometry dot plots illustrating the phenotype of TCRβ⁺CD8αSP gated cells from 3D thymic cultures.

FIG. 8G is a graph showing the percentage of CD62L⁺ CD8β⁺ cells as in FIG. 8F. Values represent mean±SEM (n=12, NS indicates no significant difference).

FIG. 8H shows flow cytometry dot plots illustrating the phenotype of iPSC differentiated in vitro for 18 days and transferred to 3D thymic culture or replaced on OP9-DL1. Flow cytometry on day 26 is shown, with one representative sample from the OP9-DL1 only group. Plots are gated on CD45⁺TCRβ⁺CD8α⁺CD62L⁺.

FIG. 9A shows flow cytometry dot plots illustrating the phenotype of Pmel-iRTE stimulated with peptide or αCD3/28.

FIG. 9B is a graph illustrating the cytokine release by Pmel-iRTE and CD3T-iRTE stimulated using αCD3/28. Values represent mean±SEM (n=3).

FIG. 9C is a graph illustrating the cytokine release by Pmel-iRTE stimulated along with natural thymocytes and splenocytes in order to measure cytokine release. Values represent mean±SEM (n=3).

FIG. 9D is a graph showing the number of Pmel-iRTE that were stimulated in vitro with cognate (gp100) or irrelevant (nucleoprotein) peptide and counted four days later. Values represent mean±SEM (n=3).

FIG. 9E is a graph showing the percentage of TCRβ+ CD8αSP cells also expressing CD8β after in vitro expansion as in FIGS. 3H and 3I. Values represent mean±SEM (n=3, NS indicates no significant difference, **** indicates P<0.0001).

FIG. 9F is a graph showing the mass (g) of mice after transfer of Pmel-iRTE or natural T cells from a spleen. Values represent mean±SD (n=7, NS indicates no significant difference).

Figure 10:
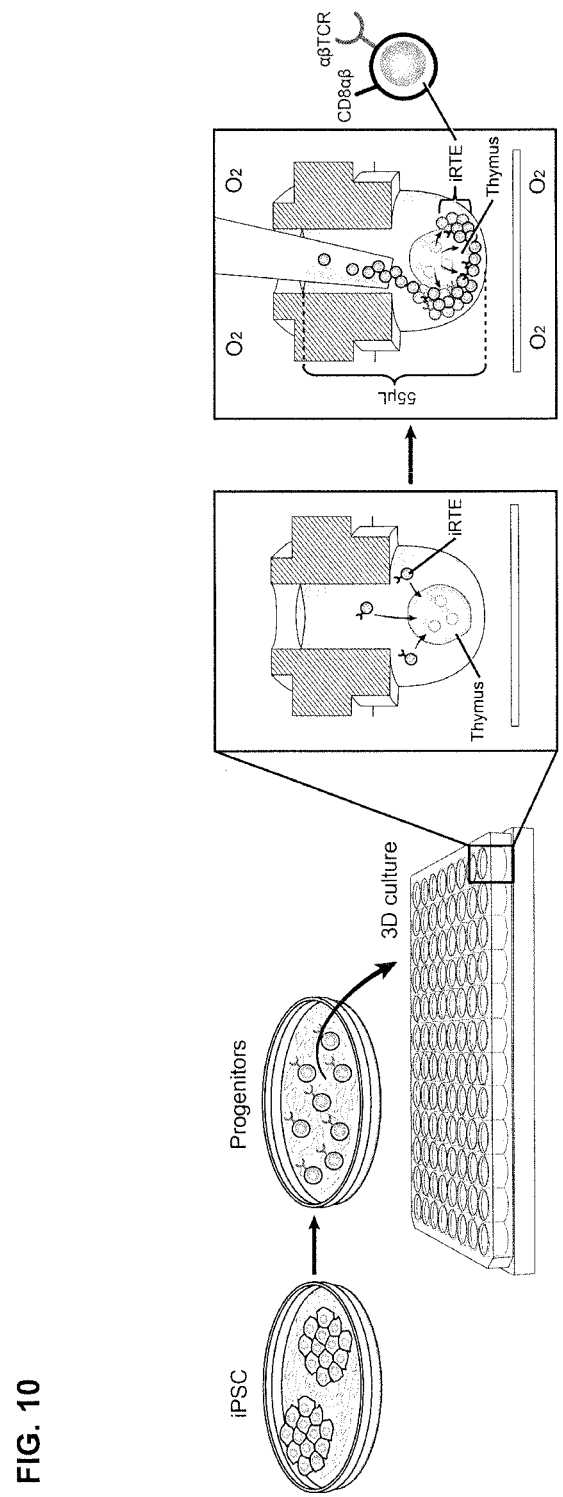

FIG. 10 is a schematic illustrating iPSC differentiation and 3D thymic culture using the PERFECTA3D hanging drop plate.

DETAILED DESCRIPTION OF THE INVENTION

An embodiment of the invention provides a method of preparing an isolated or purified population of thymic emigrant cells in vitro. The isolated or purified population of thymic emigrant cells may be included in a pharmaceutical composition useful for the treatment or prevention of a variety of different conditions as described herein.

The invention may provide many advantages. For example, the inventive methods may produce minimally differentiated T cells which may provide any one or more of increased in vivo proliferation, survival, persistence, cytotoxicity, and anti-tumor activity as compared to terminally differentiated T cells. The inventive methods may also make it possible to generate T cells having a CD4+ or CD8αβ+ single positive (SP) phenotype from source cells, e.g., pluripotent cells, e.g., induced pluripotent stem cells (iPSCs), multipotent cells, or T-lineage cells. The inventive methods may reduce or avoid the generation of T cells with an aberrant CD8αα+ or CD4−CD8α− (double negative, DN) phenotype from iPSCs.

The method may comprise modifying source cells into pluripotent cells, multipotent cells, or T-lineage cells. The source cells may be any cell of somatic origin. Examples of suitable source cells include, but are not limited to, fibroblasts, adipocytes, peripheral blood mononuclear cells (PBMCs), epithelial cells, T cells, and endothelial cells, etc. In embodiments in which the source cells are not T cells, the cells may be modified to express a T cell receptor or a chimeric antigen receptor. The source cells may be from any of the mammals described herein. Preferably, the source cells are human cells.

Preferably, the source cells are T cells. Examples of source cells may include, but are not limited to, cultured T cells, e.g., primary T cells, or T cells from a cultured T cell line, e.g., Jurkat, SupT1, etc., or T cells obtained from a mammal. If obtained from a mammal, the source cells can be obtained from numerous sources, including but not limited to blood, bone marrow, lymph node, thymus, spleen, or other tissues or fluids. Source cells can also be enriched for or purified. The T cells can be any type of T cells and can be of any developmental stage, including but not limited to, CD4+/CD8αβ+ double positive T cells, CD4+ helper T cells, e.g., Th$_1$ and Th$_2$ cells, CD4+ T cells, CD8+ T cells (e.g., cytotoxic T cells), peripheral blood mononuclear cells (PBMCs), peripheral blood leukocytes (PBLs), tumor infiltrating cells (TILs), memory T cells, naïve T cells, and the like.

In an embodiment of the invention, the source cells may have a naïve T cell (($T_N$) phenotype, central memory T cell ($T_{CM}$) phenotype, or effector memory T cell ($T_{EM}$) phenotype. The phenotypes of $T_N$, $T_{CM}$, and $T_{EM}$ cells are known in the art. For example, CCR7 and CD62L are expressed by $T_N$ and $T_{CM}$ cells, but are not expressed by $T_{EM}$ cells. The transcription factors LEF1, FOXP1, and KLF7 are expressed by $T_N$ and $T_{CM}$ cells, but are not expressed by $T_{EM}$ cells. CD45RO and KLRG1 are not expressed by $T_N$ cells, but are expressed by $T_{EM}$ cells. Gattinoni et al., *Nat. Rev. Cancer*, 12: 671-84 (2012). Alternatively or additionally, $T_N$ and $T_{CM}$ cells may be characterized by longer telomeres as compared to those of $T_{EM}$ cells.

In an embodiment of the invention, the source cells are TCRα+TCRβ+ cells. In this regard, the TCRα+TCRβ+ cells may express a functional, antigen-specific T cell receptor (TCR) including both an alpha (α) chain and a beta (β) chain. TCR alpha and beta chains are known in the art. The TCR can comprise any amino acid sequence, provided that the TCR can specifically bind to and immunologically recognize an antigen. The TCR may have antigenic specificity for any desired antigen. The phrases "antigen-specific" and "antigenic specificity," as used herein, mean that the TCR can specifically bind to and immunologically recognize an antigen, e.g., a condition-specific antigen, or an epitope thereof, such that binding of the TCR to antigen, or the epitope thereof, elicits an immune response.

The antigen-specific TCR can be an endogenous TCR, i.e., the antigen-specific TCR that is endogenous or native to (naturally-occurring on) the TCRα+TCRβ+ cell. In such a case, the TCRα+TCRβ+ cell comprising the endogenous TCR can be a TCRα+TCRβ+ cell that was isolated from a mammal which is known to express the particular condition-specific antigen. In certain embodiments, the TCRα+TCRβ+ cell is a primary T cell isolated from a mammal afflicted with a cancer. In some embodiments, the TCRα+TCRβ+ cell is a TIL isolated from a human cancer patient.

In some embodiments, the mammal from which a TCRα+ TCRβ+ cell is isolated is immunized with an antigen of, or specific for, a condition. Desirably, the mammal is immunized prior to obtaining the TCRα+TCRβ+ cell from the mammal. In this way, the isolated TCRα+TCRβ+ cells can include TCRα+TCRβ+ cells induced to have specificity for the condition to be treated, or can include a higher proportion of cells specific for the condition.

Alternatively, a TCRα+TCRβ+ cell comprising an endogenous antigen-specific TCR can be a TCRα+TCRβ+ cell within a mixed population of cells isolated from a mammal, and the mixed population can be exposed to the antigen which is recognized by the endogenous TCR while being cultured in vitro. In this manner, the TCRα+TCRβ+ cell which comprises the TCR that recognizes the condition-specific antigen, expands or proliferates in vitro, thereby increasing the number of TCRα+TCRβ+ cell having the endogenous antigen-specific receptor.

The antigen-specific TCR can be an exogenous TCR, i.e., an antigen-specific TCR that is not native to (not naturally-occurring on) the TCRα+TCRβ+ cell. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the antigen-specific TCR can be a chimeric or hybrid TCR comprised of amino acid sequences derived from TCRs from two different mammalian species. For example, the antigen-specific TCR can comprise a variable region derived from a murine TCR, and a constant region of a human TCR such that the TCR is "humanized." Methods of making recombinant TCRs are known in the art. See, for example, U.S. Pat. Nos. 7,820,174; 8,785,601; 8,216,565; and U.S. Patent Application Publication No. 2013/0274203.

A TCRα⁺TCRβ⁺ cell comprising an endogenous antigen-specific TCR can also be transformed, e.g., transduced or transfected, with one or more nucleic acids encoding an exogenous (e.g., recombinant) TCR or other recombinant chimeric receptor. Such exogenous chimeric receptors, e.g., chimeric TCRs, can confer specificity for additional antigens to the transformed TCRα⁺TCRβ⁺ cell beyond the antigens for which the endogenous TCR is naturally specific. This can, but need not, result in the production of TCRα⁺TCRβ⁺ cells having dual antigen specificities.

A TCRα⁺TCRβ⁺ cell comprising an endogenous antigen-specific TCR can also be transformed, e.g., transduced or transfected, with one or more nucleic acids encoding a "chimeric antigen receptor" (CAR). Typically, a CAR comprises the antigen binding domain of an antibody, e.g., a single-chain variable fragment (scFv), fused to the transmembrane and intracellular domains of a TCR. Thus, the antigenic specificity of a TCR can be encoded by a scFv which specifically binds to the antigen, or an epitope thereof. Methods of making such CARs are known in the art. See, for example, U.S. Pat. No. 8,465,743 and U.S. Patent Application Publication Nos. 2014/0037628 and 2014/0274909.

Any suitable nucleic acid encoding a CAR, TCR, or TCR-like protein or polypeptide can be used. In these embodiments, modifying the TCRα⁺TCRβ⁺ cells into pluripotent cells, as discussed below, can occur before, after, or simultaneously with, transformation with a CAR, TCR, or TCR-like protein or polypeptide. The CAR or TCR encoded by the transformed nucleic acids can be of any suitable form including for example, a single-chain CAR or TCR or a fusion with other proteins or polypeptides (e.g., without limitation co-stimulatory molecules).

The antigen which is recognized by the antigen-specific TCR or CAR can be any antigen which is characteristic of a condition. For example, the antigen may be, but is not limited to, a cancer antigen (also termed a tumor antigen or a tumor-associated antigen) or an infectious condition antigen, e.g., a viral antigen. Viral antigens are known in the art and include, for example, any viral protein, e.g., env, gag, pol, gp120, thymidine kinase, and the like.

The term "cancer antigen," as used herein, refers to any molecule (e.g., protein, polypeptide, peptide, lipid, carbohydrate, etc.) solely or predominantly expressed or over-expressed by a tumor cell or cancer cell, such that the antigen is associated with the tumor or cancer. The cancer antigen can be, for example, a mutated tumor antigen. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult mammal. Alternatively, the cancer antigen can be additionally expressed by stem cells or precursor cells, which cells are not normally found in an adult mammal. Cancer antigens are known in the art and include, for instance, shared tumor antigens such as, e.g., mesothelin, CD19, CD22, CD276 (B7H3), gp100, MART-1, Epidermal Growth Factor Receptor Variant III (EGFRVIII), TRP-1, KRAS, TRP-2, tyrosinase, NY-ESO-1 (also known as CAG-3), MAGE-1, MAGE-3, etc. In an embodiment of the invention, the cancer antigen is a patient-specific neoantigen. A patient-specific neoantigen may arise as a consequence of a tumor-specific mutation.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

The condition which is associated with or is characterized by the antigen recognized by the TCR or CAR can be any condition. For instance, the condition can be a cancer or an infectious condition, e.g., a viral condition, as discussed herein.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In certain preferred embodiments, the TCR or CAR has specificity for an antigen derived from melanoma. The cancer can be any cancer that expresses a cancer-specific mutated cancer antigen.

For purposes herein, "viral condition" means a condition that can be transmitted from person to person or from organism to organism, and is caused by a virus. In an embodiment of the invention, the viral condition is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. For example, the viral condition may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral condition may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

A TCRα⁺TCRβ⁺ cell comprising an antigen-specific TCR can be isolated or purified from a source using any suitable technique known in the art. For example, a TCRα⁺TCRβ⁺ cell comprising an antigen-specific TCR present in a mammalian tissue, biological fluid (e.g., blood), or in vitro culture medium can be separated from impurities, e.g., other cell types, proteins, nucleic acids, etc. using flow cytometry, immunomagnetic separation, or a combination thereof.

Modifying the source cells into pluripotent cells, multipotent cells, or T-lineage cells may be carried out in a variety of different ways. For example, modifying the source cells may comprise reprogramming the lineage of the source cells into T-lineage cells. In this regard, source cells which are not T cells or T-lineage cells may be reprogrammed to T cells or T-lineage cells. The T-lineage cells may be as described herein with respect to other aspects of the invention. For example, the method may comprise modifying source cells which are mature cancer antigen-specific T cells into less developed (immature) T cells.

Lineage reprogramming refers to the conversion of a cell from one type to another in the same lineage or a different lineage without reversion to pluripotency and is described, for example, in Jopling et al., *Nat. Rev. Mol. Cell Biol.*, 12: 79-89 (2011) and Crompton et al., *Trends Immunol.*, 35(4): 178-185 (2014). Lineage reprogramming may include, for example, transdifferentiation, dedifferentiation or transdetermination.

Transdifferentiation refers to the conversion of one mature cell type to another without a dedifferentiated or pluripotent intermediate and is described, for example, in Jopling et al., *Nat. Rev. Mol. Cell Biol.*, 12: 79-89 (2011) and Crompton et al., *Trends Immunol.*, 35(4): 178-185 (2014). An example of a method for carrying out transdifferentiation is described, for example, in Xie et al., *Cell*, 117: 663-676 (2004).

In dedifferentiation, a terminally differentiated cell reverts to a less-differentiated precursor within its own lineage. Dedifferentiation is described, for example, in Jopling et al., *Nat. Rev. Mol. Cell Biol.*, 12: 79-89 (2011) and Crompton et al., *Trends Immunol.*, 35(4): 178-185 (2014). Examples of methods for carrying out dedifferentiation are described, for example, in Yuan et al., *Science*, 335: 1195-1200 (2012) and Cobaleda et al., *Nature*, 449: 473-477 (2007).

In transdetermination, a cell dedifferentiates to an earlier progenitor (without a pluripotent intermediate) and then switches lineages to differentiate to a cell of a distinct lineage. Transdetermination is described, for example, in Crompton et al., *Trends Immunol.*, 35(4): 178-185 (2014). An example of a method for carrying out transdetermination is described, for example, in Szabo et al., *Nature*, 468: 521-26 (2010).

In an embodiment of the invention, modifying the source cells may comprise modifying the source cells to pluripotent cells or multipotent cells. Pluripotent cells have the capacity to give rise to any of the three germ layers: endoderm, mesoderm, and ectoderm. Pluripotent cells may comprise, for example, stem cells, e.g., embryonic stem cells, nuclear transfer derived embryonic stem cells, induced pluripotent stem cells, etc. Multipotent cells may comprise, for example, hematopoietic stem cells. Modifying, e.g., reprogramming, cells to a pluripotent state refers to the reversion of a cell to a pluripotent cell and is described for example, in Crompton et al., *Trends Immunol.*, 35(4): 178-185 (2014). Exemplary techniques may include somatic cell nuclear transfer (SCNT), cell-cell fusion, and direct reprogramming. Examples of methods for carrying out cell-cell fusion are described, for example, in Ogle et al., *Nat. Rev. Mol. Cell Biol.* 6: 567-75 (2005) and Zhou et al., *Cell Stem Cell*, 3: 382-388 (2008). Examples of methods for carrying out SCNT are described, for example, in Hanna et al., *Cell*, 143: 508-525 (2010); Stadtfeld et al., *Genes Dev.*, 24: 2239-2263 (2010); Wilmut et al., *Nature*, 385: 810-813 (1997); Vizcardo et al., *Cell Stem Cell*, 12: 31-36 (2013); and Crompton et al., *Cell Stem Cell*, 12: 6-8 (2013).

In an embodiment of the invention, the method may comprise modifying the source cells into induced pluripotent stem cells (iPSCs). The source cells may be modified into iPSCs in any suitable manner. Examples of methods for modifying source cells into iPSCs are described, for example, in Takahashi et al., *Cell*, 131: 861-72 (2007); Haase et al., *Cell Stem Cell*, 5: 434-441 (2009); Lowry et al., *PNAS*, 105: 2883-2888 (2008); Aasen et al., *Nat. Biotechnol.*, 26: 1276-1284 (2008); Kim et al., *Nature*, 461: 649-53 (2009); and Tsai et al., *Stem Cells*, 29: 964-971 (2011). In an embodiment of the invention, the method comprises chemically inducing pluripotent stem cells as described, for example, in Hou et al., *Science*, 341: 651-654 (2013). For example, modifying the source cells into iPSCs may comprise introducing copies of four stem cell-associated genes into the source cells. In an embodiment of the invention, the four stem cell-associated genes comprise (i) Oct 3/4, (ii) Sox 2, (iii) Klf4, and (iv) c-Myc, as described, for example, in Takahashi et al., *Cell*, 126: 663-76 (2006). In another embodiment of the invention, the four stem cell-associated genes comprise (i) Oct 3/4, (ii) Sox 2, (iii) Nanog, and (iv) LIN28, as described, for example, in Yu et al., *Science*, 318(5858): 1917-20 (2007).

In an embodiment of the invention, the source cells may be modified into pluripotent cells using genome editing techniques. Genome editing techniques can modify gene expression in a target cell by inserting, replacing, or removing DNA in the genome using an artificially engineered nuclease. Examples of such nucleases may include zinc finger nucleases (ZFNs) (Gommans et al., *J. Mol. Biol.*, 354(3): 507-519 (2005)), transcription activator-like effector nucleases (TALENs) (Zhang et al., *Nature Biotechnol.*, 29: 149-153 (2011)), the CRISPR/Cas system (Cheng et al., *Cell Res.*, 23: 1163-71 (2013)), and engineered meganucleases (Riviere et al., *Gene Ther* 21(5): 529-32 (2014)). The nucleases create specific double-stranded breaks (DSBs) at targeted locations in the genome, and use endogenous mechanisms in the cell to repair the induced break by homologous recombination (HR) and nonhomologous end-joining (NHEJ). Such techniques may be used to introduce the four stem cell-associated genes into the source cells.

Gene editing may also be useful for further modifying the cells. For example, gene editing may be used to introduce a suicide gene into the cell. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Gene editing may be used to knockdown or introduce proteins which enhance or repress T cell differentiation or antigen-specific recognition and target cell killing properties. Gene editing can be used also to knock down the receptor of certain viruses that attack T cells. For example, gene editing may be used to knockdown the receptor that the HIV virus recognizes to produce new $CD4^+$ T cells that are immune to HIV.

In another embodiment of the invention, the source cells may be modified (e.g., transduced or transfected) so as to comprise one or more nucleic acids encoding the four stem cell-associated genes. Preferably, the one or more nucleic acids is/are a recombinant nucleic acid(s). As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The terms "nucleic acid" and "polynucleotide," as used herein, refer to a polymeric form of nucleotides of any length, either ribonucleotides (RNA) or deoxyribonucleotides (DNA). These terms refer to the primary structure of the molecule, and thus include double- and single-stranded DNA, double- and single-stranded RNA, and double-stranded DNA-RNA hybrids. The terms include, as equivalents, analogs of either RNA or DNA made from nucleotide analogs and modified polynucleotides such as, though not limited to, methylated and/or capped polynucleotides. Suitable nucleotide analogs are known and are described in, e.g., U.S. Patent Application Publication 2012/0101148, and references cited therein. In an embodiment of the invention, the nucleic acid is complementary DNA (cDNA).

In certain preferred embodiments, the nucleic acid(s) encoding the stem cell-associated genes is/are carried in one or more recombinant expression vectors. The recombinant expression vector(s) can comprise any type of nucleotides, including, but not limited to DNA and RNA, which can be single-stranded or double-stranded, synthesized or obtained in part from natural sources, and which can contain natural, non-natural or altered nucleotides. The recombinant expression vector(s) can comprise naturally-occurring or non-naturally-occurring internucleotide linkages, or both types of linkages. The vector(s) may contain regulatory nucleic acid sequences which provide for expression of the stem cell-associated genes.

In some embodiments, the recombinant expression vector is a viral vector. Suitable viral vectors include, without limitation, retroviral vectors, alphaviral, vaccinial, adenoviral, adenoassociated viral, herpes viral, and fowl pox viral vectors, and preferably have a native or engineered capacity to transform T cells.

The pluripotent cells may have a stem cell phenotype including (i) the ability to self-renew and (ii) pluripotency. For example, the pluripotent cells, e.g., iPSCs may be morphologically indistinguishable from embryonic stem cells (ESCs). For example, the pluripotent cells, e.g., iPSCs may have any one or more of a round shape, large nucleolus and small volume of cytoplasm. Alternatively or additionally, the pluripotent cells, e.g., iPSCs may be any one or more of mitotically active, actively self-renewing, proliferating, and dividing. Alternatively or additionally, the pluripotent cells, e.g., iPSCs, may express any one or more of a variety of pluripotency-associated genes. Pluripotency-associated genes may include, but are not limited to, Oct-3/4, Sox2, Nanog, GDF3, REX1, FGF4, ESG1, DPPA2, DPPA4, hTERT and SSEA1. Alternatively or additionally, the pluripotent cells, e.g., iPSCs, may express any one or more of a variety of pluripotency-associated markers. For example, human iPSCs may express any one or more of the markers SSEA-3, SSEA-4, TRA-1-60, TRA-1-81, TRA-2-49/6E, and Nanog. Mouse iPSCs may express the marker SSEA-1.

The method further comprises culturing the pluripotent cells, multipotent cells, or T-lineage cells in the presence of a Notch receptor agonist to produce CD45$^+$ cells. Culturing the pluripotent cells, multipotent cells, or T-lineage cells in the presence of a Notch receptor agonist may be carried out in any suitable manner. For example, the method may comprise culturing the pluripotent cells (e.g., iPSCs) or T-lineage cells in the presence of OP9-DL1 cells as described in, for example, Lei et al., *Cell. Immunol.*, 260: 1-5 (2009) and Schmitt et al., *Nat. Immunol.*, 5: 410-17 (2004). OP9-DL1 cells are a bone-marrow-derived stromal cell line that ectopically expresses the Notch ligand, Delta-like 1 (DLL1). Notch receptor agonists may include, but are not limited to, members of the Delta-like (e.g., DLL1, DLL3, and DLL4) and the Jagged (e.g., JAG1 and JAG2) families of proteins.

The pluripotent cells, multipotent cells, or T-lineage cells may be cultured in the presence of the Notch receptor agonist for a time period sufficient to produce lymphocyte-lineage cells. Lymphocyte-lineage cells may include, for example, T-lineage cells. T-lineage cells include cells which possess at least one phenotypic characteristic of a T cell, a T cell precursor, or a T cell progenitor that distinguishes the cells from other lymphoid cells and cells of the erythroid or myeloid lineages. Such phenotypic characteristics may include, for example, expression of one or more proteins specific for T cells (e.g. CD8$^+$), or a physiological, morphological, functional, or immunological feature specific for a T cell. T-lineage cells may include, for example, T cell progenitor cells or cells committed to the T cell lineage. T-lineage cells may be characterized by the expression of any one or more of CD45, CD8α, CD8β, and CD4. Alternatively or additionally, T-lineage cells may lack MHC-I expression. Alternatively or additionally, T-lineage cells may have intermediate CD62L expression. T-lineage cells may be double positive (DP) for the expression of CD4 and CD8αβ. Preferably, T-lineage cells may be characterized by the expression of all of CD45, CD8α, CD8β, and CD4. In this regard, culturing cells in the presence of the Notch receptor agonist may produce CD45$^+$CD8α$^+$CD8β$^+$CD4$^+$ cells. The time period of culture in the presence of the Notch receptor agonist may be, for example, from about 16 days to about 21 days, about 16 days, about 17 days, about 18 days, about 19 days, about 20 days, about 21 days, or range defined by any two of the foregoing values.

The method may further comprise culturing the CD45$^+$ cells in the presence of thymic tissue, wherein culturing the CD45$^+$ cells in the presence of thymic tissue comprises migrating the cells into the thymic tissue. The cells may be cultured in the presence of thymic tissue in any suitable manner. In an embodiment of the invention, the thymic tissue may be isolated from a mammal. In an embodiment of the invention, the thymic tissue may be generated by producing thymic epithelial cells from induced pluripotent stem cells, embryonic stem cells, or by direct reprogramming. In an embodiment of the invention, the thymic tissue may be derived from thymic epithelial progenitors, third paringeal pouch epithelial cells, stromal and mesenchymal stem cells (including primitive mesoderm lineage), endothelial cells, hematopoietic stem cells and cells of a progenitor lineage (myeloids, lymphoids and erythroids), or a combination thereof. The thymic tissue may comprise thymic epithelial cells. In an embodiment of the invention, culturing the CD45$^+$ cells in the presence of thymic tissue comprises culturing the CD45$^+$ cells in the presence of thymic tissue and one or more of (i) one or more cytokines; (ii) one or more growth factors; and (iii) one or more recombinant proteins. Examples of suitable cytokines may include, but are not limited to, IL-7, Flt3L and SCF.

Preferably, culturing the CD45$^+$ cells in the presence of thymic tissue comprises culturing the cells in a three dimensional (3D) thymic culture system. Without being bound to a particular theory or mechanism, it is believed that 3D thymic tissue culture systems are more effective for facilitating T cell development as compared to thymic stromal cells in monolayer cultures (TSMCs). The 3D thymic culture system may be any 3D culture system that may maintain the thymic tissue in suspension substantially without mechanical stress to the thymic tissue. Suitable 3D thymic tissue culture systems may include, for example, fetal thymic organ cultures (FTOCs) or reaggregate thymic organ cultures (RTOCs). FTOCs are described in, for example, Nitta et al., *Basic Cell Culture Protocols, Methods in Molecular Biology*, Humana Press, Totowa, NH, pp. 85-102 (2012). In an embodiment of the invention, culturing the CD45$^+$ cells in the presence of thymic tissue comprises culturing the CD45$^+$ cells and thymic tissue in a hanging drop of medium. The culturing of the CD45$^+$ cells and thymic tissue in a hanging drop of medium may be carried out in a hanging drop plate. Hanging drop plates are commercially available such as, for example, the PERFECTA3D hanging drop plate, available from Biospherix, Parish, NY.

The thymic tissue may be any suitable thymic tissue (e.g., thymic lobes). For example, the thymic tissue may be fetal thymic tissue. The thymic tissue may be minced into a size suitable for culturing, e.g., in the hanging drop.

Culturing the lymphocyte-lineage (e.g., T-lineage (e.g., CD45$^+$)) cells in the presence of thymic tissue may comprise migrating the cells into the thymic tissue. The method may comprise seeding the thymic tissue with the lymphocyte-lineage cells. The lymphocyte-lineage cells may undergo further differentiation and development while in the thymic tissue.

The method may further comprise egressing the cells from the thymic tissue, wherein the cells egressing from the thymic tissue are thymic emigrant cells. The egressing of the cells from the thymic tissue may be observed under direct visualization using, for example, a dissecting microscope. The cells may begin to egress from the thymic tissue about 2 to about 5 days after seeding and may continue to egress for about four to about five weeks or more. It is believed that the cells may continue to egress for several months or more.

The method may further comprise isolating the thymic emigrant cells from the thymic tissue, wherein the thymic emigrant cells are CD8α$^+$CD8β$^+$CD4$^-$ or CD8α$^-$CD8β$^-$CD4$^+$. Isolating the thymic emigrant cells from the thymic tissue may be carried out in any suitable manner. For example, the method may comprise gently removing the egressing cells by removing the media from the hanging drop (e.g., by pipetting). Preferably, the isolating of the thymic emigrant cells from the thymic tissue may be carried out under direct visualization using, for example, a dissecting microscope. Preferably, the thymic emigrant cells are isolated without aspirating or disrupting the thymic tissue. The method may comprise replacing the media that was removed from the thymic tissue culture with fresh media. The thymic culture may, subsequently, be observed for the egress of further thymic emigrant cells.

The thymic emigrant cells may be CD8α$^+$CD8β$^+$CD4$^-$ or CD8α$^-$CD8β$^-$CD4$^+$. Alternatively or additionally, the thymic emigrant cells are any one or more of CCRX4$^-$, CD3$^+$, CD69$^-$, MHC-I$^+$, CD62L$^+$, and CCR7$^+$. Preferably, the thymic emigrant cells are all of CCRX4$^-$, CD3$^+$, CD69$^-$, CD62L$^+$, and CCR7$^+$. Alternatively or additionally, the thymic emigrant cells are TCRα$^+$TCRβ$^+$. Preferably, the thymic emigrant cells are TCRα$^+$TCRβ$^+$.

The method may further comprise differentiating the thymic emigrant cells into any desired type of cell. Examples of cell types which may be prepared by differentiating the thymic emigrant cells include, but are not limited to, T cells (e.g., naïve T cells, regulatory T-cells, T stem cell memory cells, effector T cells, effector memory RA cells (EMRA), Th1 cells, Th2 cells, or Th17 cells).

The inventive method may produce an isolated or purified population of thymic emigrant cells. The thymic emigrant cells prepared by the inventive methods may be useful for preparing cells for adoptive cell therapies. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

Another embodiment of the invention provides an isolated or purified population of cells prepared according to any of the methods described herein. The population of cells can be a heterogeneous population comprising the thymic emigrant cells in addition to a cell other than a thymic emigrant cell, e.g., a PBMC, a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of (e.g., consisting essentially of) thymic emigrant cells. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises thymic emigrant cells.

In an embodiment of the invention, the thymic emigrant cells are expanded in vitro prior to the administration to a mammal. Expansion of the numbers of cells can be accomplished by any of a number of methods as are known in the art as described in, for example, U.S. Pat. Nos. 8,034,334; 8,383,099; and U.S. Patent Application Publication No. 2012/0244133. For example, expansion of the numbers of cells may be carried out by culturing the cells with OKT3 antibody, IL-2, and feeder PBMC (e.g., irradiated allogeneic PBMC). In another embodiment of the invention, the thymic emigrant cells are not expanded in vitro prior to the administration to a mammal.

In an embodiment of the invention, the thymic emigrant cells are CD8α$^+$CD8β$^+$CD4$^-$ or CD8α$^-$CD8β$^-$CD4$^+$ after antigen stimulation and after expansion of the numbers of thymic emigrant cells.

The inventive populations of thymic emigrant cells can be formulated into a composition, such as a pharmaceutical composition. In this regard, the invention provides a pharmaceutical composition comprising any of the inventive populations of thymic emigrant cells described herein and a pharmaceutically acceptable carrier. The inventive pharmaceutical composition can comprise an inventive population of thymic emigrant cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive population of thymic emigrant cells, as well as by the particular method used to administer the inventive population of thymic emigrant cells. Accordingly, there are a variety of suitable formulations of the pharmaceutical composition of the invention. Suitable formulations may include any of those for oral, parenteral, subcutaneous, intratumoral, intravenous, intramuscular, intraarterial, intrathecal, or interperitoneal administration. More than one route can be used to administer the inventive population of thymic emigrant cells, and in certain instances, a particular route can provide a more immediate and more effective response than another route.

Preferably, the inventive population of thymic emigrant cells is administered by injection, e.g., intravenously. When the inventive population of thymic emigrant cells is to be administered, the pharmaceutically acceptable carrier for the thymic emigrant cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumin.

For purposes of the invention, the amount or dose of the inventive population of thymic emigrant cells or pharmaceutical composition administered (e.g., numbers of cells when the inventive population of cells is administered) should be sufficient to effect, e.g., a therapeutic or prophylactic response, in the patient over a reasonable time frame. For example, the dose of the inventive population of cells or pharmaceutical composition should be sufficient to treat or prevent a condition in a period of from about 2 hours or longer, e.g., 12 to 24 or more hours, from the time of administration. In certain embodiments, the time period could be even longer. The dose will be determined by the efficacy of the particular inventive population of cells or pharmaceutical composition administered and the condition of the patient, as well as the body weight of the patient to be treated.

Many assays for determining an administered dose are known in the art. For purposes of the invention, an assay, which comprises comparing the extent to which target cells are lysed upon administration of a given dose of such thymic emigrant cells to a mammal among a set of mammals of which is each given a different dose of the cells, could be used to determine a starting dose to be administered to a patient. The extent to which target cells are lysed upon administration of a certain dose can be assayed by methods known in the art.

The dose of the inventive population of cells or pharmaceutical composition also will be determined by the existence, nature and extent of any adverse side effects that might accompany the administration of a particular inventive population of cells or pharmaceutical composition. Typically, the attending physician will decide the dosage of the population of cells or pharmaceutical composition with which to treat each individual patient, taking into consideration a variety of factors, such as age, body weight, general health, diet, sex, inventive population of cells or pharmaceutical composition to be administered, route of administration, and the severity of the condition being treated.

Any suitable number of thymic emigrant cells of the invention can be administered to a mammal. While a single thymic emigrant cell of the invention theoretically is capable of expanding and providing a therapeutic benefit, it is preferable to administer about $10^2$ or more, e.g., about $10^3$ or more, about $10^4$ or more, about $10^5$ or more, about $10^8$ or more, T cells of the invention. Alternatively, or additionally about $10^{12}$ or less, e.g., about $10^{11}$ or less, about $10^9$ or less, about $10^7$ or less, or about $10^5$ or less, thymic emigrant cells of the invention can be administered to a mammal. The number of thymic emigrant cells of the invention can be administered to a mammal in an amount bounded by any two of the above endpoints, e.g., about $10^2$ to about $10^5$, about $10^3$ to about $10^7$, about $10^3$ to about $10^9$, or about $10^5$ to about $10^{10}$. For example, about $10^7$ to about $10^8$ thymic emigrant cells may be administered. Without being bound to a particular theory or mechanism, it is believed that the thymic emigrant cells produced by the inventive methods may be more potent than exhausted tumor infiltrating lymphocytes (TILs).

An embodiment of the invention also provides a method of treating or preventing a condition in a mammal. The method comprises administering to the mammal any of the populations of thymic emigrant cells described herein, or a pharmaceutical composition comprising any of the populations described herein, in an amount effective to treat or prevent the condition in the mammal. In an embodiment of the invention, the condition is cancer, an autoimmune condition, an infectious condition, lymphodepletion (e.g., posttransplant depletion), or thymic atrophy. The infectious condition may be, for example, a viral condition, a bacterial condition, a fungal condition, or a protozoan condition. The cancer and viral condition may be any of the cancers and viral conditions described herein with respect to other aspects of the invention.

The autoimmune condition may be any condition in which the body's immune system attacks healthy cells. Without being bound to a particular theory or mechanism, it is believed that the inventive thymic emigrant cells of the invention may be further differentiated into regulatory T cells (Tregs), which may be useful for the treatment of autoimmune conditions. Examples of autoimmune conditions which may be treated or prevented include, but are not limited to, rheumatoid arthritis, lupus, type 1 diabetes, multiple sclerosis, celiac disease, temporal arteritis, vasculitis, alopecia areata, ankylosing spondylitis, Sjögren's syndrome, and polymyalgia rheumatic.

Lymphodepletion includes the reduction or destruction of lymphocytes and T cells, e.g., by irradiation or chemotherapy, prior to treatment of a condition such as, for example, cancer. Lymphodepletion may encompass a reduced T cell repertoire, e.g., in an elderly population. Without being bound to a particular theory or mechanism, it is believed that the inventive thymic emigrant cells of the invention may be used to replace or supplement the lymphocytes and T cells lost to lymphodepletion.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a patient. Furthermore, the treatment or prevention provided by the inventive method can include treatment or prevention of one or more conditions or symptoms of the condition being treated or prevented. For example, treatment or prevention can include promoting the regression of a tumor. Also, for purposes herein, "prevention" can encompass preventing the recurrence of the condition, delaying the onset of the condition, or a symptom or condition thereof.

The term "mammal" as used herein refers to any mammal, including, but not limited to, mice, hamsters, rats, rabbits, cats, dogs, cows, pigs, horses, monkeys, apes, and humans. Preferably, the mammal is a human.

Another embodiment of the invention provides the inventive population of cells or pharmaceutical composition for use in disease modeling or therapeutic validation.

The following examples further illustrate the invention but, of course, should not be construed as in any way limiting its scope.

EXAMPLES

The following materials and methods were employed for Comparative Example 1 and Examples 1-4.

Animals

Female C57BL/6 mice were used as recipients in tumor experiments and as donors for thymic lobes. $Rag1^{-/-}$ mice (B6.12957-Rag1tm1Mom/J) were purchased from The Jackson Laboratory for in vivo expansion, bone marrow for rescue and splenocytes for antigen presenting cells. NSG mice were used for teratoma formation as a part of iPSC validation, also from The Jackson Laboratory. All animals were treated according to Institutional Animal Care and Use Committee guidelines approved for these studies at the NCI or the NHLBI.

Statistics

GRAPHPAD PRISM software was used for statistical analysis. P values of less than 0.05 were considered as significant.

Differentiation of iPSC In Vitro iPSC colonies were dissociated with 0.05% trypsin and plated on confluent OP9-DL1 at a density of $1 \times 10^5$ cells per 10-cm dish in αMEM media (Gibco) with 20% fetal calf serum (FCS), Pen/strep, vitamin C and monothiolglycerol. Culture was at 37° C. in 5% $CO_2$. On day 6, surface colonies were dissociated and the cells on confluent OP9-DL1 were replaced now with 5 ng/mL Flt3 ligand (R&D Systems) and 5 ng/mL interleukin-7 (R&D Systems). On day 11, hematopoietic progenitor cells were recovered and the cells on OP9-DL1 were replaced in 6 well plates. Cells were passaged every 4-5 days thereafter.

In Vitro Stimulation

T-lineage cells were transferred onto plates coated with αTCR antibody (Biolegend) or IgG (Biolegend) in complete media (RPMI 1640+ L-Gln with 10% FCS, sodium pyruvate, MEM-NEAA, 2-ME and Pen/strep) with 100 IU IL-2 (R&D Systems) and 5 ng/mL IL-7. After 48 hours, the cells were transferred to a new plate, and the cells were split every 2-3 days thereafter. Peptide stimulation was with $Rag1^{-/-}$ splenocytes pulsed with hgp100 (Genscript, KVPRNQDWL (SEQ ID NO: 1)) or nucleoprotein (Global Peptides).

Three Dimensional (3D) Thymic Organ Culture

C57BL/6 female mice were paired with Pepboy-J male mice, fetal thymic lobes were recovered on day 15.5 of embryonic development and cultured in 3D culture media (RPMI 1640+ L-Gln with 10% FCS, sodium pyruvate, MEM-NEAA, 2-ME and Pen/strep) supplemented with 2-deoxyguanosine at 1.35 mM (Sigma Aldrich) for 7 days at 37° C. The lobes were then transferred to a hanging drop suspension now with 5 ng/mL IL-7, Flt3L and rmSCF (R&D). Media was changed daily thereafter.

Tumor Treatment

Six-week-old female C57BL/6 mice were subcutaneously injected with $5 \times 10^5$ B16-mhgp100 melanoma cells. After 8 days, mice were irradiated with 600 Gy, randomized, and cohorts were blindly injected with cells or vehicle (PBS, $Rag1^{-/-}$ bone marrow, $2 \times 10^7$ recombinant vaccinia with hgp100). Mice had intraperitoneal injection of 200,000 IU of interleukin-2 for three days. Tumors were blindly measured every 2-3 days as a cross-sectional area for analysis.

TCR Sequencing iPSC-derived recent thymic emigrants (iRTE) were derived from the indicated iPSC lines and a BD FACS ARIA cell sorter was used to sort congenically marked CD8α single positive (SP) cells. RNA extraction and TCR sequencing were performed by iRepertoire, Inc. (Huntsville, AL). Analysis was performed using IRWEB bioinformatics tools.

Microarray Data Processing

Naïve splenocytes or iRTE were transferred into $Rag1^{-/-}$ hosts, and the cells were recovered using a BD FACS ARIA cell sorter based on expression of CD45. Total RNA was extracted using an RNEASY micro kit (Qiagen) which was reverse-transcribed, labeled and hybridized using GENECHIP Mouse Gene 2.0 ST Array following the WT pico Kit.

Data Normalization and Analysis

Probe cell intensity (.CEL) files were imported to R program (BioConductor) and normalized using the Robust Multiarray Averaging (RMA) normalization method (Irizarry et al., *Biostatistics*, 4: 249-264 (2003)). Microarray quality control was performed on the raw and normalized data. Data were analyzed using limma package, and differentially expressed genes (DEGs) were defined as genes having ≥1.5-fold change of expression in pairwise comparisons, with FDR≤0.05.

Generation of Induced Pluripotent Stem Cells from Pmel-1 Transgenic Mouse

Mouse embryonic fibroblasts (MEFs) were derived from embryonic day 12.5-13.5 Pmel-1 transgenic mice, passaged onto 12-well dishes in media containing 10% FBS and DMEM, and transduced with non-integrating Sendai virus (SeV) particles encoding OCT4, SOX2, KLF4, and c-Myc (OSKM) using the CYTOTUNE-IPS 2.0 SENDAI Reprogramming Kit (Fusaki et al., *Proc. Jpn. Acad., Ser. B, Phys. Biol. Sci.* 85: 348-362 (2009)). After three to four days, transduced Pmel-1 MEFs were passaged onto mitotically inactivated MEFs, and cultured in ES cell media containing high-glucose DMEM, 15% ESC-qualified FBS (Gibco), LIF (ESGRO), L-glutamine, non-essential amino acids, 2-mercaptoethanol, and 1.5 uM CHIR9901 (glycogen synthase kinase 3 [GSK3] inhibitor) at 37° C. with 5%. Individual iPSC colonies were picked up followed by expansion in ES cell media as previously described (Kidder, *Methods Mol. Biol.*, 1150: 227-236 (2014); Kidder et al., *Mol. Cell. Biol.*, 33: 4793-4810 (2013)). Pmel-iPSC were examined for the presence of Sendai virus using the TAQMAN iPSC Sendai Detection Kit (Applied Biosystems) by qPCR.

C57BL/6 iPSC Induction from CD3+ T Cell or Mouse Embryonic Fibroblast (MEF)

Plat-E cells were maintained as previously described (Morita, *Gene Therapy*, 7(12):1063-6 (2000); Kitamura, *Exp. Hematol.*, 31(11): 1007-14 (2003)). C57BL/6 splenic CD3+ T cells were isolated by MACS beads (Miltenyi Biotech) one day before infection, and cultured in RPMI1640 (SIGMA) containing 10% FBS (Life technologies) supplemented with DYNABEADS Mouse T-Activator CD3/CD28 (Life technologies). C57BL/6 MEFs were cultured in DMEM containing 15% FBS (SIGMA) supplemented with Retroviral preparation and transduction. Retroviral preparation was performed as previously described (Takahashi and Yamanaka, *Cell*, 126: 663-676 (2006)). Retrovirus-containing supernatants were mixed with activated T cells at $1\times10^5$ cells/ml supplemented with 10 μg/ml polybrene. The typical infection efficiency to NIH3T3 cells was 70-80%, judging by expression of a control GFP using FACSCALIBUR system (BD biosciences). The next day, media was replaced with complete T cell media, and the cells were seeded on Mitomycin C-treated MEFs. Three days after transduction, media was replaced and the culture was maintained until an ESC-like colony appeared. The ESC-like colonies were picked up and transferred to 24-well plates in Stem medium (DS Pharma Biomedical) supplemented with 2i and 0.1 mM 2ME until $5\times10^5$ cells for further experimentation. After propagation of ESC-like colony, genomic DNA was prepared to analyze rearranged TCR genes by conventional PCR. When several TCR-rearranged PCR products from one ESC-like colony were detected, re-cloning was carried out to obtain single T cell derived clone by limiting dilution culture.

iPSC Characterization

For alkaline phosphatase (AP) staining, cells were washed with PBS, fixed with 4% paraformaldehyde and then incubated with substrate (FAST RED Violet, Naphthol phosphate solution, and water in a 2:1:1 ratio) for 15-20 minutes according to the manufacturer's protocol. The staining solution was aspirated and rinsed with indicated buffer (20 mM Tris-HCL, pH 7.4, 0.15M NaCl, 0.05% Tween 20). Images were captured using a phase contrast microscope (Zeiss).

For immunocytochemistry, cells were cultured on a glass bottom dish (Thermo) and fixed with 4% paraformaldehyde in PBS for 30 min. The cells were washed with PBS, permeabilized, blocked and incubated with antibodies (1:100) for 1 hr at room temperature according to the manufacturer's protocol (Milipore SCR077). Following incubation, the cells were washed with PBS and mounted with DAPI and images were captured using a Zeiss confocal microscope (Oberkochen, Germany).

For spectral karyotyping (SKY), the ASI mouse SKY kit was used according to the manufacturer's protocol (Applied Spectral Imaging, Inc., Carlsbad, CA). Chromosomes were harvested the next day after re-plating the cells. The cells were arrested with colcemide 0.05 mkg/ml (2 hrs), followed by hypotonic treatment in KCl 0.54% at 37° C. (20 min) and fixation in ethanol/acetic acid (3:1) cold fixative (4×) (Pack and Zhuang, 2001).

Hybridization was done for 72 hrs at 37° C. in the hybridization oven followed by washes and two detection steps per manufacturer's recommendations. The slides were counterstained, mounted with DAPI/Antifade (Vector Laboratories, Burlingame, CA) and analyzed on the ZEISS IMAGER Z2 fluorescent microscope equipped with the SPECTRAL IMAGER SKY cube, using 63×-oil objective. Twenty metaphase cells were analyzed using the ASI HiSKY software.

Teratoma Formation.

Trypsinized mouse iPSCs were resuspended in PBS and 50% volume of cold Matrigel (BD Biosciences, Cat No. 354277). Cells ($0.15-1\times10^6$) were subcutaneously injected into the flanks of NSG mice (The Jackson Laboratory, Stock No. 005557) using 25 gauge needles. Three to four weeks later, the tumors (10-15 mm in diameter) were collected and fixed in 10% Formalin. Fixed tumors were embedded in paraffin, sectioned, and stained with haematoxylin and eosin (H&E).

Flow Cytometry

Fluorochrome-labeled antibodies were purchased from BD Pharmingen. The following antibody clones were used: CD3 (145-2C11), CD4 (GK1.5), CD8α (53-6.7), CD8r3 (H35-17.2), CD25 (PC61), CD44 (IM7), CD45.1 (A20), CD45.2 (104), CD62L (MEL-14), CD69 (H1.2F3), CD117 (2B8), CCR7 (4B12), MHC-I (H-2K[b], AF6-88.5), NK1.1 (PK136), IFN-γ (XMG1.2), IL-2 (554428), TCRγδ (GL3), TCRβ (H57-597), TCRVβ13 (MR12-3), TNF-α (MP6-XT22).

iPSC Passaging and Colony Expansion iPSC were cultured in Dulbecco's modified eagle medium (DMEM) with 15% lot controlled, heat-inactivated fetal calf serum (Gibco), with 2-mercaptoethanol (2-ME, Gibco 21985-023), MEM NEAA (Gibco 11140-050), Glutamax (Gibco 35050-061), Pen/strep, and leukemia inhibitory factor (Stemfactor, 03-0011-100). The iPSC were incubated in 37° C. with 5% CO2 and passaged every 2-3 days by trypsinization.

Comparative Example 1

This example demonstrates that differentiating iPSC by co-culturing the iPSC with OP9-DL1 without culturing the cells in the presence of thymic tissue generates aberrant T cells.

The efficacy of adoptive cell transfer (ACT) appears to greatly depend on the transferred T cells being in a minimally differentiated memory state, but T cells in cancer patients can be highly differentiated. One strategy to circumvent this problem is to produce new T cells for patients from autologous iPSC. iPSC lines were generated both with and without pre-rearranged αβTCR genes: Pmel-iPSC, OR-iPSC (Open Repertoire-iPSC, also referred to as Fibro-iPSC), and CD3-iPSC. A Pmel-1 T cell receptor (TCR) transgenic mouse fibroblast was reprogrammed to generate Pmel-iPSC, using non-integrating Sendai virus particles encoding OCT4, SOX2, KLF4 and C-MYC. Pmel-1 mice have an MHC class I-restricted αβTCR specific for the shared self/tumor antigen gp100, a pigment protein expressed both by non-transformed melanocytes and melanoma cancer cells (Overwijk et al., *J. Exp. Med.*, 198: 569-580 (2003); Overwijk et al., *J. Exp. Med.*, 188: 277-286 (1998)). Control iPSC lines were generated without and with pre-rearranged αβTCR genes by reprogramming a C57BL/6 fibroblast (Fibro-iPSC) and CD3+ T cell of unknown specificity (CD3T-iPSC), respectively. A C57BL/6 embryonic fibroblast with an intact TCRαβ locus was used to generate the OR-iPSC line. A control CD3-iPSC line was established from a randomly selected C57BL/6 CD3+ T cell carrying a pre-rearranged αβTCR of unknown specificity. The OR-iPSC and CD3-iPSC lines controlled for the absence or presence of pre-rearranged αβTCR genes, respectively, in the Pmel model. These iPSC lines are morphologically indistinguishable from murine embryonic stem cells (ESC). Highly sensitive polymerase chain reaction (PCR) analysis showed that Sendai virus mRNA was no longer detectable at the start of iPSC differentiation. Further, the iPSC expressed the pluripotency-associated genes Oct-4, Sox2, Dppa2 and SSEA1. In order to assess chromosomal integrity and potentially detect subtle chromosomal translocations, which can lead to hematologic malignancies (Veldman et al., *Nat. Genet.*, 15: 406-410 (1997)), ultra-high resolution spectral karyotyping (SKY) was performed, and it was found that iPSCs exhibited a normal pattern. Finally, whether iPSC could form teratomas with three germ layers upon injection into NSG mice was tested, and their pluripotency was confirmed.

It was next sought to test if the iPSC lines were capable of generating T cells and whether the presence of pre-rearranged αβTCR genes influenced their development. Similar to the approach used by other groups (Lei et al., *Cell. Immunol.*, 260: 1-5 (2009); Schmitt et al., *Nat. Immunol.*, 5: 410-417 (2004)), the OP9-DL1 co-culture system, which provides extrinsic Notch signaling, was used to induce iPSC differentiation into T-lineage cells (FIG. 1A). During the process of iPSC differentiation, the continuous generation of heterogeneous populations of off-lineage progeny were observed. For example, on day 10, colonies of beating primordial cardiomyocytes were regularly observed on OP9-DL1 stromal layers, presumably derived from a primitive mesodermal precursor.

After 16 days of differentiation, CD45$^+$ hematopoietic progenitor cells derived from iPSC were predominantly double negative (DN) but a minor population started to express CD4 and CD8α (FIGS. 6A and 6B). Between days 18 and 21, most CD45$^+$ cells gained expression of CD4 and/or CD8α (FIGS. 1B, 1C, and 6C). It was previously shown that mice derived from a T cell nucleus have aberrant expression of pre-rearranged αβTCR genes early in development (Serwold et al., *J. Immunol.*, 179: 928-938 (2007)). Similarly, early expression of TCRβ in iPSC with pre-rearranged αβTCR genes (i.e. Pmel-iPSC and CD3T-iPSC) was observed, but there was no evidence of an altered rate of differentiation or proliferation (FIGS. 1B and 1D). Like their natural counterparts, double positive (DP) T cells from iPSC were CD8αβ$^+$, had intermediate CD62L expression and lost MHC-I expression (FIGS. 6C-6F). These experiments indicated that iPSC with and without rearranged αβTCR genes were capable of differentiating on OP9-DL1 into DP T cells with a phenotype similar to that of natural DP thymocytes.

During normal thymopoiesis, positively selected DP T cells can mature into CD4-CD8α$^+$ (CD8α single positive, CD8αSP) T cells. On day 18 of iPSC differentiation in vitro, it was observed that some cells were indeed CD8αSP (FIGS. 6C and 7A) and, furthermore, had absent expression of CD69. Seen on natural thymocytes, this pattern indicates that the CD8αSP T cells are mature and poised for emigration to the periphery (Hogquist et al., *J. Immunol.*, 195: 1351-1357 (2015)). However, while natural CD8αSP have high expression of MHC-I, CD8αSP T cells derived from iPSC were strangely MHC-I negative (FIG. 7A). Other markers including CD8β$^+$ and CD62L, strongly expressed by normal CD8αSP T cells, were abnormal in the iPSC-derived cells (FIG. 6C). It was anticipated that these superficial phenotypic anomalies were indicative of major underlying differences in T cell biology.

The CD8αSP T cells from days 18-26 were used in these analyses. These CD8αSP T cells grown using established techniques are referred to as Extrathymic T Cells.

In order to gain insight into the programs of T cells produced in OP9-DL1, Pmel-iPSC were differentiated for 18 days in OP9-DL1, were stimulated with a combination of antigen presenting cells and peptide, and then analyzed 8 days later, using naïve splenocytes as a control (FIG. 1E). The cells expanded specifically to peptide (FIG. 7B) and released cytokines in response to stimulation (FIG. 7C), which indicated that they were mature and functional. However, during expansion, they lost surface expression of CD8β and adopted CD8αα$^+$ or DN phenotypes (FIGS. 1F and 1G). The CD8αα$^+$ phenotype is sometimes seen when immature self-reactive T cells bind strongly to self-antigens, perhaps as a mechanism to prevent harmful autoimmunity (Yamagata et al., *Nat. Immunol.*, 5: 597-605 (2004)). For that reason, αTCR antibody was used to induce positive selection (Takahama et al., *Nature*, 371: 67-70 (1994)), but the T cells still adopted CD8αα$^+$ or DN phenotypes and sometimes gained high expression of the innate immune marker NK1.1, which is not normally seen on CD8αβ$^+$ peripheral T cells (FIGS. 7D and 7E). These functional studies provided additional evidence that CD8αSP T cells generated from iPSC on OP9-DL1 are quite dissimilar from natural CD8αSP splenocytes.

To further interrogate the differences between endogenous CD8αSP T cells and those produced from iPSC by OP9/DLL1, a transcriptional analysis of naïve CD8+ T cells and Extrathymic T Cells was performed by RNA-sequencing (RNA-seq), identifying 2,462 differentially expressed genes (log 2FC>2, adjusted P-value<0.01). A systems biology approach was used to identify transcriptional differences in the regulation of biological pathways using the Over Representation Analysis vs. the Accumulated Perturbation Analysis (Tarca et al., *Bioinformatics* 25, 75-82 (2009)) (STAR Methods). The analysis performed on differentially expressed genes identified 21 significantly different pathway terms. Three pathways with clinical relevance to ACT were identified: antigen processing and presentation, graft vs. host disease and allograft rejection. An investigation of genes within these pathways revealed that Extrathymic T Cells had decreased expression of classical MHC-I (H2-D1 and H2-K1) and non-classical MHC genes (H2-Q4, H2-T3, H2-T10, H2-Q7, H2-Ob, H2-DMb 1 and H2-DMa), as well as increased expression of natural killer receptors (Klrc1, Klrc2, Klrc3). The downregulation of MHC class I genes, as well the upregulation of Ptcra, Rag1, Rag2 and Rorc, suggest that Extrathymic T Cells have an immature T cell phenotype potentially due to an inadequate positive selection, impaired TCR signaling or an unfinished allelic exclusion program (Carpenter and Bosselut, *Nat. Immunol.*, 11: 666-673 (2010); Hogquist et al., *J. Immunol.*, 195: 1351-1357 (2015); von Boehmer, *Nat. Rev. Immunol.*, 5: 571-577 (2005)). Thus, Extrathymic T Cells execute aberrant transcriptional programs that diverge from those of physiologically differentiating naïve CD8$^+$ T cells. The results indicated that Extrathymic T Cells generated by OP9/DLL1 were characterized by gene deviations including high NK cell markers, low 'classical' MHC-I and persistent expression of Rag genes. These qualities suggested that the cells simply had not experienced physiologic developmental cues. The results suggest that Extrathymic T Cells generated by OP9/DLL1 do not pass positive selection.

Example 1

This example demonstrates that T-lineage cells from iPSC develop in a 3D thymic culture and spontaneously egress.

It was reasoned that since T cells produced on OP9-DL1 had no obvious phenotypic abnormalities until after the DP T cell stage, perhaps they were being subjected to inappropriate signals for survival and selection. In order to restore the physiologic signals present during thymopoiesis, a 3D thymic culture system was used to recapitulate a thymic microenvironment in vitro (FIG. 2A) (Nitta et al., *Basic Cell Culture Protocols, Methods in Mol. Biol.*, Humana Press pp. 85-102 (2012)). Day 15.5 embryonic thymic lobes were depleted of virtually all endogenous lymphocytes by treatment with the cytotoxic agent 2-deoxyguanosine. Then, iPSC were differentiated for 18 days on OP9-DL1 to produce T-lineage cells, which were seeded into 3D cultures with or without thymic lobes. 3D cultures with only a depleted thymus (FIG. 2B) or only T-lineage cells (FIG. 2B)

showed no evidence of T cell maturation or proliferation (FIGS. 8A and 8B). In contrast, after 4-10 days, the thymuses that had been seeded with T-lineage cells developed halos of homogenous appearing mononuclear cells. These iPSC-derived recent thymic emigrants are referred to as "iRTE". From a single seeding of 1×10$^3$ T-lineage cells, some 3D thymic cultures exuded iRTE continuously for over 3 weeks. Using cytofluorometry, the presence of cells with forward- and side-scatter that were in a lymphocyte like-gate and that were of the TCRβ$^+$ CD8αSP T cell phenotype was verified. Neither the fetal thymic lobes nor iPSC-derived immature T cells alone showed any evidence of T cell maturation or proliferation. These observations show that iPSC-derived T-lineage cells have the biophysical capacity to migrate into a depleted thymus and egress spontaneously after several days.

To test whether iPSC-derived T lineage cells were indeed migrating deep into the thymic lobes, the co-cultured tissues were sectioned. Histological analysis of unseeded control lobes showed a tissue architecture characterized by an astrocyte-like thymic epithelial web, but no CD3+ cells. When seeded with iPSC-derived immature T cells, the tissue was repopulated with CD3+ mononuclear cells. This confirmed iPSC-derived T cells' capacity to migrate and repopulate thymic lobes devoid of endogenous T cells. Hematoxylin and eosin staining of the thymic lobe with and without seeding of iPSC-derived immature T cells and confocal images of sectioned lobes stained with DAPI (nucleus) and CD3 (T cell) showed that iTE are produced inside the thymic tissue.

The thymus lobes were crushed along with the surrounding cells, and a mix of DP T cells and single positive T cells was found (FIG. 8C). Most of the CD8αSP T cells inside the lobes were CD8β$^+$CD62L$^+$CD69$^-$ and MHC-I$^+$, indicating that they have successfully passed the positive selection process. Later, gentle pipetting was used to recover iRTE in the halo around the thymus without shearing the cortex. Using this approach, nearly pure populations of iRTE were recovered, which exhibited a mature single positive phenotype (CD8α$^+$CD4$^-$, gated on CD45$^+$TCRβ) (FIG. 2C). Fibro-iPSC, which lack pre-rearranged αβTCR genes, generated iRTE including a diverse mix of DN, TCRβ$^+$CD4$^+$ CD8α$^-$ (CD4SP) and CD8αSP T cells. In contrast, Pmel-iPSC and CD3T-iPSC have pre-rearranged αβTCR genes and produced iRTE that were predominantly CD8αSP (FIGS. 2C-2E and 8C). These results were consistent with the hypothesis that iPSC with a pre-rearranged MHC-I-restricted TCR would only produce CD8+ T cells after thymic education. This prompted a sort of CD8αSP iRTE in order to analyze their αβTCR repertoires by deep sequencing. Fibro-iRTE had a diverse beta TCR repertoire, but Pmel-iRTE showed one dominant clonal beta TCR chain (>98%). Consistent with studies showing that alpha TCR rearrangements continue until positive selection (Borgulya et al., *Cell*, 69: 529-537 1992), it was found that alpha TCR locus rearrangements in Pmel-iRTE were present at a low level. These results show that Fibro-iPSC can produce CD4$^+$ or CD8αβ$^+$ iRTE with a broad TCR repertoire, whereas Pmel-iPSC have pre-rearranged αβTCR genes that largely suppress recombination events as they develop into iRTE.

It was suspected that iRTE were progressing through normal stages of thymic development in the 3D culture system, so it was sought to compare their phenotypes with those of natural thymocytes from an adult mouse (Hogquist et al., *J. Immunol.*, 195: 1351-1357 (2015)). Multicolor flow cytometry with congenic markers and a dump gate consisting of NK1.1, TCRγδ, CD44 and CD25 was used in order to exclude natural subsets of unconventional T cells (natural killer cells, γδ T cells and CD4$^+$ T regulatory cells) that arise during normal thymic development (Xiong and Raulet, *Immunol. Rev.*, 215: 15-31 (2007)). Flow cytometry was used to measure markers important for T cell differentiation and maturation including MHC-I, L-selectin (CD62L) and CD69. It was found that a small percentage of iRTE (1-2%) were positive for NK1.1 or TCRγδ. The majority of iRTE had a surface phenotype consistent with mature thymocytes, exhibited low levels of the acute activation marker CD69 and had gained high levels of MHC-I and CD62L which are associated with high proliferative competency, cytokine production, survival and lymphoid homing in the periphery (FIGS. 3A-3F and 8C-8G). Unlike T-lineage cells continuously cultured in OP9-DL1, iRTE also expressed the chemokine receptor CCR7, an essential molecule for trafficking and migration by mature T cells (FIG. 8H). These observations suggest that iRTE had progressed through normal stages of thymic development and adopted a phenotype similar to that of mature thymocytes.

Robust expansion of Extrathymic T Cells specific to cognate peptide stimulation failed to occur, and this proliferative defect was corrected with thymic education. Pmel-iRTE capacity to rapidly expand >1000 fold in vitro was analogous to naïve CD8+ T cells. Pmel-iRTE maintained CD8αβ+ expression after prolonged re-stimulation. These results indicated that thymic education corrected the aberrant downregulation of key markers like MHC-I and CD8β+ expression with preservation of proliferative capacity.

Example 2A

This example demonstrates that iRTE exhibit normal cytokine release and in vitro expansion.

Analysis by flow cytometry showed that the iRTE of Example 1 have a natural phenotype, but a deeper evaluation of cellular programs can be gained from functional studies. Cytokine production (IL-2, TNFα, and IFN-γ) was evaluated by Pmel-iRTE in vitro using peptide or αCD3/28, and it was found that they are functional and specific to cognate peptide (FIGS. 3G and 9A). αCD3/28 was used to stimulate Pmel-iRTE and CD3T-iRTE, and it was found that their cytokine release profiles were nearly identical (FIG. 9B). Finally, cytokine production was directly compared by Pmel-iRTE, natural CD8αSP thymocytes and naïve splenocytes (FIG. 9C). Compared with thymocytes, iRTE released similar amounts of IL-2 but more TNF-α; neither released significant quantities of IFN-γ, which is thought to promote peripheral tolerance (Hogquist et al., *J. Immunol.*, 195: 1351-1357 (2015)). Compared with naïve peripheral splenocytes, iRTE released considerably more IL-2. Together, these data were interpreted as suggesting that iRTE were in a developmental stage more advanced than CD8αSP thymocytes, and one distinct from naïve splenocytes.

Comparative Example 1 showed that T-lineage cells produced on OP9-DL1 lost expression of CD8β after stimulation and became CD8αα$^+$ or DN T cells. In order to test whether iRTE exhibited similar changes, they were subjected to peptide stimulation conditions with natural splenocytes as a comparison. After five days, CD8αβ$^+$ iRTE and splenocytes expanded in vitro hundreds of fold (FIG. 3H). The expansion was specific to cognate but not irrelevant peptide (FIG. 9D). After expansion, iRTE retained high expression of the CD8β molecule (FIGS. 3I and 9E), with the post-expansion CD8β$^+$CD62L$^-$ phenotype gated on CD8α$^+$ being 97% for splenocytes, 15% for T-lineage cells, and 95% for iRTE. These experiments revealed that iRTE generated by 3D cultures have the ability to expand in vitro to a similar magnitude as CD8αβ+ splenocytes, and retain a normal phenotype when doing so.

To interrogate the differences between endogenous CD8αSP T cells and iRTE on a whole transcriptome level, RNA-seq was used. Using this approach, 2,059 differentially expressed genes were identified (log 2 FC>2, adjusted p-value<0.01). First, to examine whether iRTE execute aberrant transcriptional programs like those observed in Extrathymic T Cells, the differentially expressed genes included in the three clinical relevant pathways previously selected were analyzed. iRTE displayed upregulation of genes associated with activation (Gzmb, Ifng and IL2), which can be associated with recent thymic maturation and subsequent activation due to extrinsic IL-7 in the 3D culture system media. iRTE displayed upregulation of IL4, Hspa2, and CD80. iRTE displayed downregulation of H2-Q7, Prf1, H2-Q4, Cd86, H2-Q6, H2-Q10, H2-T10, H2-Aa, H2-T3, H2-Ob, H2-Eb1, Cd74, and H2-Ab1. Additionally, genes aberrantly regulated in Extrathymic T Cells, including downregulation of classical MHC complex genes and upregulation of NK receptors, were rectified in iPSC-derived iRTE after thymic education. Notably, unlike Extrathymic T Cells, iRTE show loss of immature T cell markers (Ptcra, Rag1, Rag2 and Rorc) and upregulation of classical MHC-I post-selection markers (H2-K1 and H2-D1). Furthermore, the iRTE clustered with naïve T cells, indicating their completion of the positive selection stage. Taken together, these results are consistent with the idea that iRTE had completed positive selection and have corrected key abnormalities found in Extrathymic T Cells.

Example 2B

This example demonstrates that whole transcriptome analysis reveals a shift in iRTE gene expression towards a naïve CD8+ T cell program.

To further probe the transcriptional differences between iPSC-derived T-lineage cells with and without thymic education (i.e., iRTE and Extrathymic T Cells), the expression of a curated list of 102 genes known to be important for T cell ontogeny, thymocyte activation, and memory formation were compared (Best et al., *Nat. Immunol.*, 14: 404-412 (2013); Hogquist et al., *J. Immunol.*, 195: 1351-1357 (2015); Schmitz et al., *Int. Immunol.*, 15: 1237-1248 (2003)). These gene expression patterns were then compared with primary naïve CD8+ Pmel T cells and with double positive T lineage cells differentiated using OP9/DLL1 (0P9-DP). Using hierarchical clustering and correlation of sequenced samples, it was found that iRTE and naïve T cells clustered together, and were distinct from cells matured in the absence of thymic education. It was also surprising to find that DP and CD8αSP T cells derived in OP9/DLL1 were strikingly similar. In an attempt to clarify the identity of this novel population of cells, the activated signaling pathways and upstream regulators in iRTE vs. Extrathymic T Cells were analyzed by Gene Set Enrichment Analysis (GSEA) and Ingenuity Pathway Analysis (IPA). GSEA identified enrichment of signaling pathways associated with positive selection and endogenous Recent Thymic Emigrant (RTE) development, including the activation of IFN, NFκB and TNF pathways and downregulation of E2F signaling pathways (Carpenter and Bosselut, *Nat. Immunol.*, 11: 666-673 (2010); Xing et al., *Nat. Immunol.*, 17: 565-573 (2016)). Moreover, IPA showed an enrichment of similar regulatory pathways in iRTE, including activation of IFN pathway genes, as well as activation or inhibition of upstream regulators correlating to changes in activity which have been associated with late stage thymocyte maturation (Xing et al., *Nat. Immunol.*, 17: 565-573 (2016)). Thus, iRTE exhibited transcriptional profiles observed in late stages of thymic maturation and RTE development.

To understand in more detail the developmental stage of iRTE, key genes marking the transition from mature CD8αSP thymocytes to the naïve stage were selected, and the expression patterns of OP9-DP, Extrathymic T Cells, iRTE and CD8αSP naïve T cells were compared (Carpenter and Bosselut, *Nat. Immunol.*, 11: 666-673 (2010); Fink, *Annu. Rev. Immunol.*, 31: 31-50 (2013); Hogquist et al., *J. Immunol.*, 195: 1351-1357 (2015)). It was found that iRTE closely clustered with naïve CD8αSP T cells in genes important for post-thymic selection and RTE peripheral maturation, and displayed a unique expression pattern of genes related to thymic egression. Collectively, RNA-seq data confirm that Extrathymic T Cells have a transcriptional program similar to that of immature DP thymocytes, while iRTE, which have been subjected to thymic education, constitute a unique population of cells that are transcriptionally similar to naïve CD8αSP T cells.

Example 3

This example demonstrates that iRTE launch effector T cell programs that are nearly identical to naturally-occurring T cells.

Based on phenotypic and functional data, it was speculated that iRTE would behave in vivo similarly to naïve splenocytes from a Pmel-1 mouse. In order to test the capacity of iRTE to restore immunity under lymphopenic conditions, equivalent numbers of either Pmel-iRTE or naïve splenocytes were transferred into lymphocyte-deficient Rag1$^{-/-}$ hosts (FIG. 4A). After four weeks, transferred cells in both groups retained high expression of the CD8β molecule, differentiated into CD44+CD62L− effector memory T cells (FIGS. 4B and 4C) and expanded to a similar magnitude (FIG. 4D). Similar numbers of progeny T cells within the spleens of mice receiving iRTE or physiologically produced naïve T cells were found. This finding indicated that one could find a nearly two-log increase in the cells that were transferred over 4 weeks of expansion in vivo, however it remained unknown whether these massively expanded cells retained functionality. The ability of progeny cells recovered from the spleens of recipient mice to produce cytokines upon specific stimulation with cognate peptide was measured. In addition to phenotype and expansion, transferred iRTE and naïve splenocytes developed an effector cytokine release profile, characterized by the secretion of low amounts of IL-2 and high amounts of IFN-γ (FIG. 4E). Similar patterns of cytokine production between ex vivo expanded iRTE and naïve T cells were observed. Quantitatively, many progeny cells produced IFN-γ and TNFα, and relatively fewer made IL-2. Notably, all recipient mice remained healthy without any evidence of weight loss, autoimmunity or lymphomagenesis at a follow-up of more than 180 days (FIG. 9F). Teratoma formation was not observed. These data showed that iRTE behave in vivo quite similarly to natural CD8αβ+ T cells.

During these functional studies, subtle differences in IL-2 production were observed between iRTE and naïve T cells (FIG. 9C). While no major phenotypic or functional differences were detected after immune reconstitution in vivo, it was sought to more sensitively compare the biology of iRTE and naïve T cells by evaluating whether they initiated similar programs in vivo. For this, microarray analysis was used to study the expression of genes essential for T cell activation and memory formation (Blair et al., *Nat. Immunol.,* 14: 404-412 (2013)). A significant correlation between iRTE and naïve T cells was found by both RNA-seq (R2=0.952) and microarray analyses (Figure S6B, R2=0.983). Because of early concerns of loss of classical major histocompatibility class-1 (MHC-I) loss using iRTE-derived cells, RPKM values H2-K1 and H2-D1 were closely examined, which end up being transcriptionally equivalent to naïve T cells. Most of these transcripts were expressed at similar levels, including Gzmb, Prf1, Tbx21, Id2, Klf3, Klf2, Gata3, Zeb2, Prdm1, Tcf3, Ifng, Bcl6, Foxo3, Ctla4, Il2, Myb, Tnf, Pdcd1, Cd44, Foxo1, Eomes, Il2ra, Cd69, and Il7r. However, there were several differentially expressed genes related to memory formation, including Id3, Bcl-2, IL12rb2, Sell and Myc. This finding is consistent with data showing that natural recent thymic emigrants have a reduced capacity for memory formation compared to naïve T cells (Fink, *Annu. Rev. Immunol.,* 31: 31-50 (2013)). A global transcriptional analysis using all 41,345 microarray probes was also performed, which revealed that 151 named genes were differentially expressed. Thus, these results are interpreted as showing that iRTE initiate similar programs in vivo as naturally occurring T cells, and have a gene expression profile that is consistent with a recent thymic emigrant stage of development.

As another measure of in vivo properties, whether iRTE could be used to treat mice with large established B16 melanoma tumors was tested (FIG. 5A). Cohorts of mice received Pmel-iRTE, CD3T-iRTE, unconventional T cells (FIGS. 5B and 5C) generated from Pmel-iPSC, naïve splenocytes, or vehicle. Mice that received CD3T-iRTE had no treatment benefit relative to control mice who received radiation and IL-2 but no cell transfer. Similarly, mice that received unconventional T cells from Pmel-iPSC also had no anti-tumor benefit compared to control. In contrast, transfer of only 5×10$^4$ Pmel-iRTE resulted in significant suppression of tumor growth (P=0.028) and prolongation of animal survival (P=0.0004) compared with mice receiving CD3T-iRTE or unconventional T cells (FIGS. 4B and 4C). It is remarkable that Pmel-iRTE recovered from 3D thymic cultures achieved tumor destruction comparable with freshly explanted naïve splenocytes, the gold standard in previous models (Klebanoff et al., *PNAS,* 102: 9571-76 (2005)). It should be noted that Pmel-iRTE were not as efficient as naturally-occurring T cells at this small dose, especially in the mice measured blindly 24 days after adoptive cell transfer (Pmel-iRTE vs. Pmel-Naïve P=0.009). Thus, iRTE constitute a novel homogenous population of in vitro generated tumor-antigen specific T cells from iPSC with a pre-arranged TCR. iRTE do not display the classical developmental aberrations observed in T cells generated by OP9/DLL1 culture system and demonstrate a rejuvenated capacity to expand, persist in vivo and mediate regression of solid tumors. These outcomes demonstrated that small numbers of cancer antigen-specific iRTE are capable of mediating anti-tumor function in vivo and prolonging the survival of recipient mice.

Example 4

This example demonstrates advantages of using a three dimensional (3D) thymic environment such as, for example, the PERFECTA3D hanging drop plate (3D Biomatrix, Inc., Ann Arbor, MI) in a method of preparing an isolated or purified population of thymic emigrant cells in vitro as compared to alternative vessels.

Methods of preparing an isolated or purified population of thymic emigrant cells in vitro were attempted in a variety of vessels, as shown in Table 1.

TABLE 1

| | Suspension* | Media volume | Gas exchange** | Versatility*** | Visualization**** |
|---|---|---|---|---|---|
| 96-well plate | no | 200 uL | low | high | limited |
| Classical hanging drop plate | yes | 20 uL | high | low | limited |
| Air-flow culture | no | 0.5-3.0 mL | high | low | moderate |
| 30 culture (PERFECTA3D hanging drop plate) | yes | 55 uL | high | high | good |

*Suspension: eliminates cell-plastic mechanical interaction and promotes the natural aggregation of cells without centrifugation or mechanical manipulation
**Gas exchange: proximity of cells and thymus to the liquid-gas interface where diffusion can occur
***Versatility: ease of cellular seeding, media change, and cellular recovery
****Visualization: ability to directly visualize individual cells by light microscopy The 96-well plates were limited by poor visibility and limited gas exchange. It was also suspected that T cell development in the 96-well plate was altered by mechanical signals due to contact with plastic.

In order to prevent physical contact-mediated signaling between the thymic lobes and a solid surface, the method was attempted in a classical hanging-drop plate. Classical hanging drop plates used an inverted Terazaki plate in order to be able to manipulate the cultures. Classical hanging drop plates are described in Nitta et al., "The Development of T Lymphocytes in Fetal Thymus Organ Culture," in: Helgason et al. (Eds.), *Basic Cell Culture Protocols, Methods in Molecular Biology,* Humana Press, Totowa, NJ, pp. 85-102 (2012). However, the unwieldy and unstable nature of the classical hanging drop plates were limiting for continuous culture monitoring, daily media changes, and the constant micro-manipulation necessary for cell recovery.

Drawing from recent advances in 3D-culture technology used for embryoid body formation and 3D tumor microtissue culture, a PERFECTA3D hanging drop plate was co-opted to make the 3D thymic culture system (FIG. 10). The PERFECTA3D hanging drop plate enabled high-throughput FTOC, wherein a single researcher could closely monitor and efficiently maintain dozens of individual cultures at a given time. The PERFECTA3D hanging drop plate had the strengths of the traditional hanging drop plate, including suspension culture, maximal oxygen exchange (as the aggregates lie at the air-media interface), ease of visualization, and micro-manipulation under light microscopy. The drops were stable and were able to be accessed from above, which greatly facilitated media changes and cellular recovery by direct pipetting under a microscope. This allowed media to be changed several times a day without mechanical disruption and permitted the continual harvesting of solely the T cells that egress from the lobes. PERFECTA3D hanging drop plates are described in, for example, "3D Cell Culture: An Early-Stage Oncology Drug Discovery Tool," White Paper, 3D BIOMATRIX Three-Dimensional Cell Culture (2012).

Methods of preparing an isolated or purified population of thymic emigrant cells in vitro may involve making slight changes in media and monitoring the cells under the microscope. The classical hanging drop plate cannot be monitored under a microscope because the base of the Terazaki plate prevents the light from going through the drop. Moreover, the Terazaki plate holds very small drops (20 µl), which may become exhausted easily and stress the cells and the thymic tissue, which may decrease the quality of the culture.

not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: synthetic

<400> SEQUENCE: 1

Lys Val Pro Arg Asn Gln Asp Trp Leu
1               5
```

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does

The invention claimed is:

1. A method of preparing an isolated or purified population of thymic emigrant cells in vitro, comprising:
   modifying T cells that have antigenic specificity for a cancer antigen into pluripotent cells, multipotent cells, or T-lineage cells;
   culturing the pluripotent cells, multipotent cells, or T-lineage cells in the presence of a Notch receptor agonist to produce $CD45^+$ cells;
   culturing the $CD45^+$ cells in the presence of thymic tissue in a hanging drop of medium, wherein culturing the $CD45^+$ cells in the presence of thymic tissue comprises seeding the thymic tissue with the $CD45^+$ cells and migrating the cells into the thymic tissue;
   egressing the cells from the thymic tissue in the hanging drop of medium, wherein the cells egressing from the thymic tissue are thymic emigrant cells and wherein the cells begin to egress from the thymic tissue 2 to 5 days after seeding the thymic tissue with the $CD45^+$ cells; and
   isolating the thymic emigrant cells from the thymic tissue without disrupting the thymic tissue, wherein the thymic emigrant cells are $CD8\alpha^+CD8\beta^+CD4^-$ or $CD8\alpha^{31}CD8\beta^-CD4^+$, wherein the thymic emigrant cells have the capacity to differentiate into a T cell with a T cell receptor having antigenic specificity for the cancer antigen, and wherein the thymic emigrant cells do not express Ptcra, Rag1, Rag2 and Rorc.

2. The method according to claim 1, wherein the T cells are TCRα⁺TCRβ⁺ cells.

3. The method according to claim 1, wherein the T cells are CD4+CD8αβ+ double positive (DP) cells.

4. The method according to claim 1, wherein the T cells have a naïve T cell ($T_N$) phenotype, central memory T cell ($T_{CM}$) phenotype, or effector memory T cell ($T_{EM}$) phenotype.

5. The method according to claim 1, wherein culturing cells in the presence of the Notch receptor agonist produces CD45⁺CD8α⁺CD8β⁺CD4⁺ cells.

6. The method of claim 1, wherein the thymic emigrant cells are any one or more of CD69⁻, MHC-I⁺, CD62L⁺, and CCR7⁺.

7. The method of claim 1, wherein the thymic emigrant cells are TCRα⁺TCRβ⁺.

8. The method of claim 1, further comprising differentiating the thymic emigrant cells into naïve T cells, T stem cell memory cells, effector T cells, effector memory RA cells (EMRA), Th1 cells, Th2 cells, or Th17 cells.

9. The method of claim 1, further comprising differentiating the thymic emigrant cells into regulatory T cells.

10. The method of claim 1, further comprising differentiating the thymic emigrant cells into T cells with a T cell receptor having antigenic specificity for the cancer antigen.

* * * * *